United States Patent
Werbovetz et al.

(12) 
(10) Patent No.: US 6,706,754 B2
(45) Date of Patent: Mar. 16, 2004

(54) REVERSED AMIDINES AND METHODS OF USING FOR TREATING, PREVENTING, OR INHIBITING LEISHMANIASIS

(75) Inventors: Karl A. Werbovetz, Worthington, OH (US); James J. Brendle, Beltsville, MD (US); David W. Boykin, Atlanta, GA (US); Chad E. Stephens, Villa Rica, GA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/985,590

(22) Filed: Nov. 5, 2001

(65) Prior Publication Data

US 2002/0156098 A1 Oct. 24, 2002

Related U.S. Application Data

(60) Provisional application No. 60/288,428, filed on May 4, 2001, provisional application No. 60/246,330, filed on Nov. 7, 2000, and provisional application No. 60/246,244, filed on Nov. 6, 2000.

(51) Int. Cl.$^7$ .......................... A61K 31/38; A61K 31/34; A61K 31/155

(52) U.S. Cl. ......................... 514/438; 514/461; 514/631; 514/634

(58) Field of Search ................................. 514/634, 438, 514/468, 631

(56) References Cited

U.S. PATENT DOCUMENTS

| | | | |
|---|---|---|---|
| 4,622,330 A | 11/1986 | Bochis et al. | 514/313 |
| 5,202,320 A | 4/1993 | Tidwell et al. | 514/218 |
| 5,594,138 A | * 1/1997 | Dysktra et al. | 540/596 |
| 5,602,172 A | * 2/1997 | Boykin et al. | 514/461 |
| 5,639,755 A | * 6/1997 | Dykstra et al. | 514/256 |
| 6,030,946 A | 2/2000 | Klaus et al. | 514/12 |

FOREIGN PATENT DOCUMENTS

| | | |
|---|---|---|
| WO | 96/40737 | 12/1996 |
| WO | 02/057224 | 7/2002 |

OTHER PUBLICATIONS

Das et al., "Synthesis and Antiprotozoal Activity of 2,5–Bis(4–guanylphenyl)thiophenes and –pyrroles", Journal of Medicinal Chemistry (1977), vol. 20, No. 9. (see abstract).*

Karen L. Goa et al., "Pentadidine Isethionate, A Review of its Antiprotozoal Activity, Pharmacokinetic Properties and Therapeutic Use in Pneumocystis Carinii Pneumonia", Drugs, (1987), vol. 33, pp. 242–258.

Isabelle Hellier et al., "Treatment of Old World Cutaneous Leishmaniasis by Pentamidine Isethionate", Dermatology (2000), vol. 200, pp. 120–123.

V.H. Hodgkinson et al., "Leishmania Amazonensis: Cultivation and Characterization of Axenic Amastigote–Like Organisms", Experimental Parasitology, (1996), vol. 83, No. 1, pp. 94–105.

T.K. Jha et al., "Miltefosine, an Oral Agent, For the Treatment of Indian Visceral Leishmaniasis", The New England Journal of Medicine, (1999), vol. 341, No. 24, pp. 1795–1800.

M. Joshi et al., Mol. Biochem. Parasitol., (1993), vol. 58, pp. 345–354.

A. Kumar et al., Heterocyclic Comm., (1999), vol. 5, pp. 301–304.

R. Lira et al., J. "Evidence that the High Incidence of Treatment Failures in Indian Kala–Azar Is Due to the Emergence of Antimony–Resistant Strains of Leishmania Donovani", Infect. Dis., (1999), vol. 180, pp. 564–567.

C. Ling et al., "Models for Intramolecular Exchange in Organic –Conjugated Open–Shell Systems: 3–Nitrenophenyl and 4–Nitrenophenyl Units Connected by 2,5–Furandiyl, 2,5–Thiophenediyl, and 2,5–Pyrrolediyl Nonalternant Exchange Linkers", J. Am. Chem. Soc., (1994), vol. 116, No. 19, pp. 8784–8792.

Alan J. Magill et al., "Visceral Infection Caused by Leishmania Tropica in Veterans of Operation Desert Storrn", New England Journal of Medicine, (1993), vol. 328, No. 19, pp. 1383–1387.

Susan Méndez et al., "Leishmania Infantum: Infection of Macrophages in Vitro with Promastigotes", International Journal for Parasitology, (1996), vol. 26, No. 6, pp. 619–622.

P.L. Olliaro et al., "Practical Progress and New Drugs for Changing Patterns of Leishmaniasis", Parasitol Today, (1993), vol. 9, No. 9, pp. 323–328.

J.C. Phillips et al., Fd. Chem Tox., (1990), vol. 28, No. 5, pp. 375–394.

(List continued on next page.)

*Primary Examiner*—Kevin E. Weddington
(74) *Attorney, Agent, or Firm*—Elizabeth Arwine

(57) ABSTRACT

Methods for treating, preventing or inhibiting leishmaniasis in a subject comprising administering to the subject a therapeutically effective amount of at least one compound having the structural formula

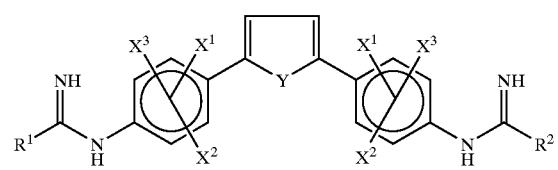

wherein Y is a heteroatom; $R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group are disclosed.

29 Claims, 9 Drawing Sheets

OTHER PUBLICATIONS

J. Seaman et al., "The Epidemic of Visceral Leishmaniasis in Western Upper Nil, Southern Sudan: Course and Impact from 1984 to 1994", International Journal of Epidemiology, (1996), vol. 25, No. 4, pp. 862–871.

D.E. Seitz et al., "Synthesis and Reactivity of the 2,5–BIS(Trimethylstannyl) Derivatives of Thiopene and Furan", Synthetic Communications, (1983), vol. 13, No. 2, pp. 121–128.

Berry G. Shearer et al., "S–2–Naphthylmethyl Thioacetimidate Hydrobromide: A New Odorless Reagent for the Mild Synthesis of Substituted Acetamidines", Tetrahedron Letters, (1997), vol. 38, No. 2, pp. 179–182.

Aden C. Smith et al., "Activity of the Novel Immunomodulatory Compound Tucaresol Against Experimental Visceral Leishmaniasis", Antimicrobial Agents and Chemotherapy, (2000), vol. 44, No. 6, pp. 1494–1498.

Jaime Soto et al., "Successful Treatment of Colombian Cutaneous Leishmaniasis with Four Injections of Pentamidine", Am. J. Trop. Med. Hgy., (1994), vol. 50, pp. 107–111.

Edgar A. Steck et al., "Leishmania Donovani, Plasmodium Berghel, Trypanosoma Rhodesiense: Antiprotozoal Effects of Some Amidine Types", Exp. Parasitol, (1981), vol. 52, No. 3, pp. 404–413.

C.E. Stephens et al., "Diguanidino and "Reversed" Diamidino 2,5–Diarylfurans as Antimicrobial Agents", J. Med. Chem., (2001), vol. 44, pp. 1741–1748.

Weiguo Su, "A Convenient Synthesis of DI–(Benzyloxycarbonyl)–Protected Guanidines", Synthetic Communications, (1996), vol. 26, No. 2, pp. 407–413.

S. Sundar et al., "Short–Course of Oral Miltefosine for Treatment of Visceral Leishmaniasis", Clin. Infect. Dis., (2000), vol. 31, pp. 1110–1113.

S.F. Varenikova et al., "Methoxylation of 3,4–Dinitrochloro(Bromo)Benzene", J. Org. Chem., (1985), vol. 21, pp. 1651–1652.

K. Werbovetz et al., "Purification, Characterization, and Drug Susceptibility of Tubulin from Leishmania", Mol. Biochem. Parasitol., (1999), vol. 98, pp. 53–65.

Antonio Alcina et al., "Activity of P536, a UDP–Glucose Analog, Against Trypanosoma Cruzi", Antimicrobial Agents and Chemotherapy, (1988), vol. 32, No. 9, pp. 1412–1415.

E.D. Amstutz, "Studies in the Sulfone Series. VII. The Preparation of 2,8–Diaminophenoxathiin–5–Dioxide and Bis–(2–Hydroxy–4–Aminophenyl) Sulfone", J. Am. Chem. Soc., (1950), vol. 72, pp. 3420–3423.

M. Bajic et al., Heterocyclic Comm., (1996), vol. 2, p. 135.

M. Basselin et al., "Altered Transport Properties of Pentamidine–Resistant Leishmania Donovani and L. Amazonensis Promastigotes", Parasitol Res., (1997), vol. 83, pp. 413–418.

J.D. Berman et al., Rev. Infect. Dis., (1988), vol. 10, No. 3, pp. 560–586.

J.D. Berman, "Human Leishmaniasis: Clinical, Diagnostic, and Chemotherapeutic Developments in the Last 10 Years", Clin. Infect. Dis., (1997), vol. 24, pp. 684–703.

D.W. Boykin et al., "Dicationic Diarylfurans as Anti–Pneumocystis Carinii Agents", J. Med. Chem., (1995), vol. 38, pp. 912–916.

Mar Calonge et al., "Effects of Cationic Diamidines on Polyamine Content and Uptake on Leishmania Infantum in In Vitro Cultures", Biochemical Pharmacology, (1996), vol. 52, pp. 835–841.

K.P. Chang, "Human Cutaneous Leishmania in a Mouse Macrophage Line: Propagation and Isolation of Intracellular Parasites", Science, (1980), vol. 209, No. 4462, pp. 1240–1242.

J.L. Collins et al., "N–Phenylamidines as Selective Inhibitors of Human Neuronal Nitric Oxide Synthase: Structure–Activity Studies and Demonstration of in Vivo Activity", J Med. Chem., (1998) vol. 41., pp. 2858–2871.

Isaac O. Donkor et al., "Trypanocidal Activity of Dicationic Compounds Related to Pentamidine", Eur. J. Med. Chem., (2001), vol. 36, pp. 531–538.

L. Razzak et al., 1992, "Acquired Immune Deficiency Syndrome Amidino Phenoxy Pentane", 2 pages.

Katherine T. Hopkins et al., "Extended Aromatic Furan Amidino Derivatives as Anti–Pneumocystis Carinii Agents", J. Med. Chem. (1998) 41:3872–3878.

Chad E. Stephens et al., "Diguanidino and "Reversed" Diamidino 2,5–Diarylfurans as Antimicrobial Agents" J. Med. Chem. (2001) 44:1741–1747.

R. Kirk et al., "The Use of Certain Aromatic Diamidines in the Treatment of Kala–Azar", pp. 181–197.

Constance A. Bell et al., "Structure–Activity Relationships of Analogs of Pentamidine against Plasmodium Falciparum and Leishmania Mexicana Amazonensis" Antimicrobial Agents and Chemotherapy (1990) 34(7):1381–1386.

Edgar A. Steck et al., "Leishmania Donovani, Plasmodium Berghei, Trypanosoma Rhodesiense: Antiprotozoal Effects of Some Amidine Types" Exper. Parasitol. 52:404–413:404–413.

James J. Brendle et al., "Antileishmanial Activities of Several Classes of Aromatic Dications" Antimicrobial Agents and Chemotherapy (2002) 46(3):797–807.

\* cited by examiner

| Compound | Structure | | | | | | | Axenic Activity μg/ml | Macrophage Activity μg/ml L. donovani | Macrophage Activity μg/ml L. mexicana | Toxicity μg/ml |
|---|---|---|---|---|---|---|---|---|---|---|---|
| | Y | $X^1$ | $X^2$ | $X^3$ | $R^1$ | | $R^2$ | | | | |
| 1DWB667 4a | O | H | H | H | 2-Pyridinyl | | 2-Pyridinyl | 0.550 ± 0.038 | 0.942 ± 0.384 | 1.371 ± 0.264 | 4.281 ± 1.149 |
| DB 611 4d | O | H | H | H | Methyl $CH_3$ | | Methyl $CH_3$ | >100 | NA | NA | NA |
| DB 613 4b | O | H | H | H | Phenyl | | Phenyl | 60.519 | NA | NA | NA |
| DB 626 4e | O | H | Methyl $CH_3$ | H | Phenyl | | Phenyl | NA | NA | NA | NA |
| DB 656 4c | O | H | H | H | Cyclohexyl | | Cyclohexyl | NA | NA | NA | NA |
| DB 680 | O | H | H | H | $NH_2$ | | $NH_2$ | 1.463 ± 0.095 | NA | NA | NA |
| DB 702 4f | O | H | Methyl $CH_3$ | H | 2-Pyridinyl | | 2-Pyridinyl | 0.174 ± 0.024 | 0.063 ± 0.050 | 0.220 ± 0.090 | 2.234 ± 0.210 |
| DB 709 4i | O | H | Methoxy $OCH_3$ | H | 2-Pyridinyl | | 2-Pyridinyl | 0.157 ± 0.062 | 0.104 ± 0.002 | 0.127 | 0.199 ± 0.009 |

Fig. 1

| | | | | | | | | |
|---|---|---|---|---|---|---|---|---|
| DB 710 4h | O | H | Methyl Methyl CH₃ | H | 5-Methyl-2-pyridinyl | 0.242 ± 0.053 | 0.530 ± 0.171 | 0.094 ± 0.044 | 3.642 ± 0.193 |
| DB 712 4j | O | H | Cl | H | 2-Pyridinyl | 0.308 ± 0.046 | 0.127 | 0.689 ± 0.069 | 3.387 ± 0.472 |
| DB 713 | S | H | Methyl CH₃ | H | 2-Pyridinyl | 0.324 ± 0.062 | 0.385 ± 0.206 | 0.371 ± 0.127 | >0.781 |
| DB 714 4k | O | Methyl CH₃ | Methyl CH₃ | H | 2-Pyridinyl | 0.290 ± 0.112 | 0.246 ± 0.091 | 0.359 ± 0.176 | >1.56 |
| DB 716 | O | H | Methyl CH₃ | H | 2-quinolyl | 10.404 | NA | NA | NA |
| 4g | Y | Methyl CH₃ | H | H | 6-Methyl-2-pyridinyl | 12.716 | NA | NA | NA |
| DB 749 | | | | | | | | | |
| DB 752 6e | S | H | Methyl CH₃ | H | NH₂ | 0.708 ± 0.372ᵃ | NA | NA | NA |
| DB 762 6a | O | H | Ethoxy | H | NH₂ | 3.160 ± 1.480ᵃ | NA | NA | NA |
| DB 763 6c | O | H | H | Methoxy OCH₃ | NH₂ | 2.630 ± 0.360ᵃ | NA | NA | NA |

Fig. 1 cont.

| | | | | | | | |
|---|---|---|---|---|---|---|---|
| DB 766 4l | O | H | Propan-2-oxy | H | 2-Pyridinyl | 2-Pyridinyl | 0.153 ± 0.055[a] | NA | NA | NA |
| DB 778 6b | O | H | Propan-2-oxy | H | NH$_2$ | NH$_2$ | 3.670 ± 0.920 | NA | NA | NA |
| DB 779 6d | O | H | H | Ethoxy | NH$_2$ | NH$_2$ | 2.630 ± 0.260 | NA | NA | NA |
| DB 785 4n | O | H | H | Ethoxy | 2-Pyridinyl | 2-Pyridinyl | 0.787 ± 0.005 | NA | NA | NA |
| DB 786 4m | O | H | Propan-2-oxy | H | 5-Methyl-2-pyridinyl | 5-Methyl-2-pyridinyl | 0.478 ± 0.279 | NA | NA | NA |
| DB 715 | | | | | R = (2-pyridinyl carboximidamide) | | 9.644 ± 2.007 | NA | NA | |
| DB 739 | | | | | R = (carbamimidamide) | | 3.266 ± 0.296 | NA | NA | |

Fig. 1 cont.

| | | | | | |
|---|---|---|---|---|---|
| DB 740 | ![structure] | R = ![amidine] | 2.227 ± 0.142 | NA | NA | NA |
| DB 745 | ![structure] | R = ![pyridyl] | 0.198 ± 0.085 | NA | NA | NA |
| DB 747 | ![structure] | R = ![pyridyl] | 1.757 ± 0.043 | NA | NA | NA |
| DB 748 | ![structure] | R = ![amidine] | 2.139 ± 0.058 | NA | NA | NA |

Fig. 1 cont.

| | | | | | |
|---|---|---|---|---|---|
| DB 750 |  | R =  | 1.483 ± 0.003 | NA | NA | NA |
| DB 751 |  | R =  | 6.842 ± 0.921 | NA | NA | NA | a Mean ± standard deviation from at least two independent experiments.

Plate # 6329

Amastigote Drug Assay

1DWB 667 (ng/ml)

| Sample | Concentration | Units | Values |
|---|---|---|---|
| 3D1 | 100000.0 | ng/ml | 0.061 |
| 3D2 | 50000.0 | ng/ml | 0.060 |
| 3D3 | 25000.0 | ng/ml | 0.061 |
| 3D4 | 12500.0 | ng/ml | 0.059 |
| 3D5 | 6250.0 | ng/ml | 0.058 |
| 3D6 | 3125.0 | ng/ml | 0.062 |
| 3D7 | 1562.5 | ng/ml | 0.060 |
| 3D8 | 781.3 | ng/ml | 0.075 |
| 3D9 | 390.6 | ng/ml | 0.475 |
| 3D10 | 195.3 | ng/ml | 0.510 |
| 3D11 | 97.7 | ng/ml | 0.510 |

A = 0.510
B = 8.440
C = 523.205
D = 0.060
R2 1.000

| $y = ((A - D)/(1 + (x/C)^B)) + D$: | A | B | C | D | R^2 |
|---|---|---|---|---|---|
| ○ Drug 3 (1DWB 667: Concentratiion vs Values) | 0.51 | 8.44 | 523.205 | 0.06 | 1 |

REVERSED AMIDINES AND METHODS OF USING FOR TREATING, PREVENTING, OR INHIBITING LEISHMANIASIS

CROSS REFERENCE TO RELATED APPLICATIONS

This application is related to U.S. Provisional Patent Application No. 60/288,428, filed May 4, 2001, naming Karl A. Werbovetz, James J. Brendle, David W. Boykin, and Chad E. Stephens as co-inventors, U.S. Provisional Patent Application No. 60/246,330, filed Nov. 7, 2000, naming Karl A. Werbovetz, James J. Brendle, David W. Boykin, and Chad E. Stephens as co-inventors, and U.S. Provisional Patent Application No. 60/246,244, filed Nov. 6, 2000, naming Karl A. Werbovetz, James J. Brendle, David W. Boykin, and Chad E. Stephens as co-inventors, all of which are herein incorporated by reference in their entirety.

ACKNOWLEDGMENT OF GOVERNMENT SUPPORT

This invention was jointly made by employees of the United States Army and Georgia State University. The government has rights in the invention.

BACKGROUND OF THE INVENTION

1. Field of the Invention

This invention relates generally to a method of treating, preventing or inhibiting leishmaniasis in a subject. In particular, the invention relates to a method of treating, preventing or inhibiting leishmaniasis in a subject by the administration of at least one reversed amidine.

2. Description of the Related Art

Parasitic diseases have an overwhelming impact on public health in developing areas of the world. One such disease is leishmaniasis, a spectrum of disease in man that is life-threatening in its most severe form. Leishmaniasis is caused by several species of Leishmania. These unicellular organisms of the order Kinetoplastida are related to trypanosomes, the causative organisms of Sleeping Sickness in Africa and Chagas' disease in South America. Leishmania parasites commonly exist in two distinct forms, the motile promastigote of the insect vector and the sessile amastigote present in the mammalian host. Promastigotes are transmitted to humans by the bite of infected phlebotomine sandflies, which are found throughout the world's inter-tropical and temperate regions. Upon delivery into the mammalian host, promastigotes infect macrophages of the reticuloendothelial system and transform into amastigotes.

Three main clinical variants of this disease are known: cutaneous, mucocutaneous, and visceral. Cutaneous leishmaniasis can manifest itself as a single skin ulceration at the site of the sandfly bite appearing soon after infection or month later as disseminated lesions. Mucocutaneous syndrome develops as the cutaneous form, but progresses months or years later to lesions of the mouth, nose, or pharynx. The major long-term effects of cutaneous and mucocutaneous disease are scarring. Visceral leishmaniasis has an incubation period of 3–6 months and involves the reticuloendothelial system.

Clinical manifestations include enlargement of the liver and spleen, fever, anemia, and weight loss. Symptomatic visceral disease often ends in death in the absence of treatment. In recent years, the coexistence of HIV and Leishmania species causing visceral disease has resulted in several hundreds of cases of dually infected individuals. See Berman, J. D., (1997) Clin. Infect. Dis. 24:684. The World Health Organization recently estimated in 2000 that leishmaniasis affects people in 88 countries, with 350 million at risk of contracting the disease and about two million new cases each year. The devastating impact of this disease is exemplified by the recent epidemic of visceral leishmaniasis in the Sudan, which claimed an estimated 100,000 lives. See Seaman, J., et al. (1996) Int. J. Epidemiol. 25:862. This disease is frequently a threat in military operations, as demonstrated by the outbreak of viscerotropic leishmaniasis during the Gulf War. See Magill, J., et al. (1993) N Engl J Med 328:1383.

Unfortunately, few drugs or compounds exist which exhibit anti-leishmanial activity in vitro or in vivo. Pentavalent antimonial compounds have been the first line drugs for leishmaniasis since the 1940's, and two forms of Sb(V) are commonly used. Sodium stibogluconate (Pentostam® (Wellcome Foundation, London, England)) and meglumine antimoniate (Glucantime® (Rhone Poulenc, Paris, France)) are prescribed according to Sb(V) content and are generally considered to be equivalent in terms of efficacy and toxicity. These drugs must be given by injection over a 20–28 day course. Unfortunately, the antimonial compounds exhibit side effects such as nausea and severe toxic side effects, such as hepatitis, nephritis, and myocarditis. See Berman, J. D., (1997). Further, reports of unresponsiveness to antimony treatment are becoming more frequent. See Olliaro, P., et al. (1993) Parasitol. Today 9:323. Moreover, there is a strong correlation between clinical resistance to Pentostam® and decreased in vitro susceptibility to this drug. See Lira, R., et al. (1999) J. Infect. Dis. 180:564.

Amphotericin B is also used as a treatment for visceral leishmaniasis. Past implementation of this drug was limited to toxic side reactions including fever, bone pain, and decreased renal function. Although new clinical formulations of amphotericin B in lipid complexes are less toxic than amphotericin B, these new clinical formulations are more expensive, and a major problem in treating visceral leishmaniasis in developing countries. Also, amphotericin B and amphotericin B-lipid complexes do not appear to be suitable for treating nonvisceral disease. See Berman, J. D., (1997). Oral miltefosine has shown some promise in the treatment of visceral leishmaniasis in India, however, efficacy against cutaneous disease has yet to be reported and miltefosine has not yet been approved for clinical use in any country. See Jha, T., et al. (1999) N. Eng. J. Med. 341:1795 and Sundar, S., et al. (2000) Clin. Infect. Dis. 31:1110.

Other compounds such as pentamidine and analogues thereof exhibit some anti-leishmanial activity. See U.S. Pat. No. 5,202,320; Steck, E. A., et al. (1981) Exp. Parasitol. 52(3):404–413; and Berman, J. D., et al. (1988) Rev. Infect. Dis. 10(3):560–586. Pentamidine is frequently used for the treatment of leishmaniasis and is currently being evaluated by the U.S. Army for use on troops infected with Leishmania. See Hellier, I., et al. (2000) Dermatology 200:120 and Soto, J., et al. (1994) Am. J. Trop. Med. Hyg. 50:107. However, the drawbacks of the clinical use of pentamidine and pentamidine analogues are the route of administration (injection) and the toxicity of the compounds. Administration by injection increases the expense of the treatment and makes the use of the drug less practical in developing nations where cost is a major factor. The clinical side effects of pentamidine include renal and hepatic toxicity, pancreatitis, hypotension, dysglycemia, and cardiac abnormalities. See Berman, J. D., (1997) and Goa, K., et al. (1987) Drugs 33:242.

Thus, a need exists for an anti-leishmanial agent for the treatment of leishmaniasis.

SUMMARY OF THE INVENTION

The present invention generally relates to compounds and methods for the treatment of leishmaniasis.

In some embodiments, the present invention provides a method for treating, preventing or inhibiting leishmaniasis in a subject comprising administering to the subject a therapeutically effective amount of at least one compound having the structural formula

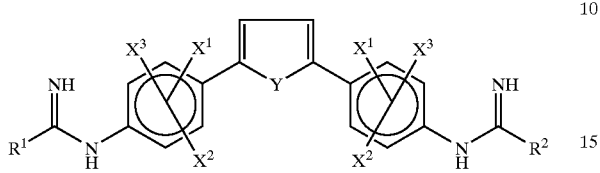

wherein Y is a heteroatom; $R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group. In preferred embodiments, Y is O or S, $R^1$ and $R^2$ are independently H, phenyl, cyclohexyl, quinolyl, pyridinyl, or methylpyridinyl, and $X^1$, $X^2$, and $X^3$ are independently H, Cl, amino, methyl, methoxy, ethoxy, or propan-2-oxy. Preferably, $X^1$, $X^2$, and $X^3$ are each independently at positions 2, 3, 5, or 6 of the phenyl rings, more preferably, $X^1$ and $X^2$ are each independently at positions 2 or 3. Preferably, the subject is mammalian, more preferably, the subject is human.

In some embodiments, the method further includes administering a supplementary active compound to the subject. The supplementary active compound may be sodium stibogluconate such as Pentostam®, meglumine antimoniate such as Glucantime®, pentamidine, amphotericin B, miltefosine, paromomycin, and the like.

In preferred embodiments, the compound is
2,5-Bis[4-(2-pyridylimino)aminophenyl]furan;
2,5-Bis[4-(benzimidoylamino)phenyl]furan;
2,5-Bis[4-(cyclohexylimino)aminophenyl]furan;
2,5-Bis[4-(acetimidoyl)aminophenyl]furan;
2,5-Bis[4-(benzimidoyl)amino-2-methylphenyl]furan;
2,5-Bis[2-methyl-4-(2-pyridylimino)aminophenyl]furan;
2,5-Bis[2-methyl-4-(2-quinolylimino)aminophenyl]furan;
2,5-Bis[2-methyl-4-(5-methyl-2-pyridylimino)aminophenyl]furan;
2,5-Bis[2-methoxy-4-(2-pyridylimino)aminophenyl]furan;
2,5-Bis[2-chloro-4-(2-pyridylimino)aminophenyl]furan;
2,5-Bis[2,6-dimethyl-4-(2-pyridylimino)aminophenyl]furan;
2,5-Bis(4-guanidino-2-methylphenyl)furan;
2,5-Bis(4-guanidino-2-trifluoromethylphenyl)furan;
2,5-Bis[2-methyl-4-(2-pyridylimino)aminophenyl]thiophene;
2-[5(6)-(2-Pyridylimino)amino-2-benzimidazoyl]-5-[4-(2-pyridylimino)aminophenyl]furan;
2,5-Bis[2-methyl-4-(2-quinolylimino)aminophenyl]furan;
2-(4-Guanidinophenyl)-4-(3-guanidinophenyl)furan;
2,5-Bis(4-guanidino-2,6-dimethylphenyl)furan;
2,5-Bis[2-ethoxy-4-(2-pyridylimino)aminophenyl)furan;
2,5-Bis[2,3-dimethyl-4-(2-pyridylimino)aminophenyl]furan;
2,5-Bis(4-guanidino-2,3-dimethylphenyl)furan;
2,5-Bis[2-methyl-4-(6-methyl-2-pyridylimino)aminophenyl]furan;
2,5-Bis[2-hydroxy-4-(2-pyridylimino)aminophenyl]furan;
2,5-Bis[2-methoxy-5-(2-pyridylimino)aminophenyl]furan;
2,5-Bis[2-(2-propoxy)-4-(2-pyridylimino)aminophenyl]furan;
2,5-Bis[2-(2-propoxy)-4-(5-methyl-2-pyridylimino)aminophenyl]furan;
2,5-Bis[3-ethoxy-4-(2-pyridylimino)aminophenyl]furan;
2,5-Bis(2-ethoxy-4-guanidinophenyl)furan;
2,5-Bis[4-guanidino-2-(2-propoxy)phenyl]furan;
2,5-Bis(4-guanidino-3-methoxyphenyl)furan;
2,5-Bis(3-ethoxy-4-guanidinophenyl)furan;
2,5-Bis[3-methoxy-4-(2-pyridylimino)aminophenyl]furan
2,5-Bis(4-guanidino-2-methylphenyl)thiophene; or
2,5-Bis(4-guanidinophenyl)thiophene.

In some embodiments, the present invention relates to a method for treating, preventing or inhibiting leishmaniasis in a subject comprising administering to the subject a therapeutically effective amount of at least one reversed amidine. Preferably, the subject is mammalian, more preferably, human.

In some embodiments, the present invention relates to a method for treating, preventing or inhibiting leishmaniasis in a subject comprising administering to the subject a therapeutically effective amount of at least one compound comprising at least one reversed amidine group having the structural formula

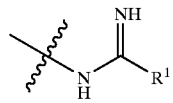

wherein $R^1$ is H or an alkyl, cycloalkyl, heterocycloalkyl, aryl, amino or heteroaryl group. Preferably, the subject is mammalian, more preferably, human.

In other embodiments, the present invention provides a method for treating, preventing or inhibiting a disease or disorder associated with leishmaniasis in a subject comprising administering to the subject a therapeutically effective amount of at least one compound having the structural formula

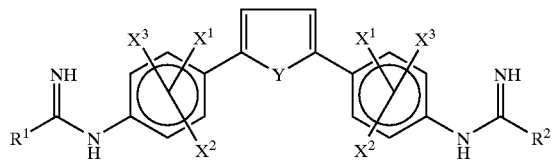

wherein Y is a heteroatom; $R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group. In preferred embodiments, Y is O or S, $R^1$ and $R^2$ are independently H, phenyl, cyclohexyl, quinolyl, pyridinyl, or methylpyridinyl, and $X^1$, $X^2$, and $X^3$ are independently H, Cl, amino, methyl, methoxy, ethoxy, or propan-2-oxy. Preferably, $X^1$, $X^2$, and $X^3$ are each independently at positions 2, 3, 5, or 6 of the phenyl rings, more preferably, $X^1$ and $X^2$ are each independently at positions 2 or 3. The disease or disorder may be cutaneous leishmaniasis, mucocutaneous leishmaniasis, or visceral leishmaniasis. Preferably, the subject is mammalian, more preferably, human.

In some embodiments, the present invention relates to a method of reducing, suppressing or inhibiting an amount of a parasite in a target comprising administering to the target an effective amount of at least one compound having the structural formula

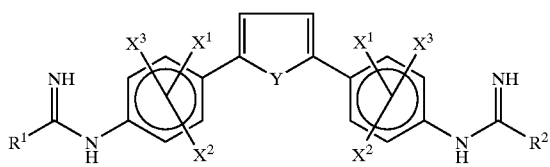

wherein Y is a heteroatom; $R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group. In preferred embodiments, Y is O or S, $R^1$ and $R^2$ are independently H, phenyl, cyclohexyl, quinolyl, pyridinyl, or methylpyridinyl, and $X^1$, $X^2$, and $X^3$ are independently H, Cl, amino, methyl, methoxy, ethoxy, or propan-2-oxy. Preferably, $X^1$, $X^2$, and $X^3$ are each independently at positions 2, 3, 5, or 6 of the phenyl rings, more preferably, $X^1$ and $X^2$ are each independently at positions 2 or 3. In preferred embodiments, the reversed amidine compound reduces, suppresses or inhibits parasite growth, infection, or proliferation by about 50% at a concentration of about 10.0 μg/ml or less, about 7.0 μg/ml or less, about 5.0 μg/ml or less, about 2.5 μg/ml or less, or about 1.0 μg/ml or less. In preferred embodiments, the parasite is a Leishmania parasite. In other preferred embodiments, the compound reduces, suppresses or inhibits L. mexicana by about 50% at a concentration of about 10.0 μg/ml or less, preferably less than about 1.0 μg/ml. In other embodiments, the compound reduces, suppresses or inhibits L. donovani at a concentration of about 10.0 μg/ml or less, preferably less than about 1.0 μg/ml. In some preferred embodiments, the reverse amidine compound reduces, suppresses, or inhibits Leishmania parasite growth, infection, or proliferation by about 50% at a concentration of about 0.1 μg/ml to about 1.0 μg/ml. The target is a mammal or tissues or cells derived therefrom. Preferably, the mammal is human.

In other embodiments, the present invention provides a pharmaceutical composition for treating, preventing or inhibiting leishmaniasis in a subject comprising a therapeutically effective amount of at least one compound having the structural formula

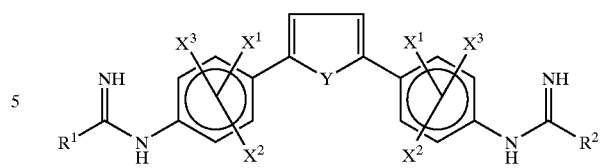

wherein Y is a heteroatom; $R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group. In preferred embodiments, Y is O or S, $R^1$ and $R^2$ are independently H, phenyl, cyclohexyl, quinolyl, pyridinyl, or methylpyridinyl, and $X^1$, $X^2$, and $X^3$ are independently H, Cl, amino, methyl, methoxy, ethoxy, or propan-2-oxy. Preferably, $X^1$, $X^2$, and $X^3$ are each independently at positions 2, 3, 5, or 6 of the phenyl rings, more preferably, $X^1$ and $X^2$ are each independently at positions 2 or 3. Preferably, the subject is mammalian, more preferably the subject is human.

In some embodiments, the present invention provides a kit comprising at least one compound having the structural formula

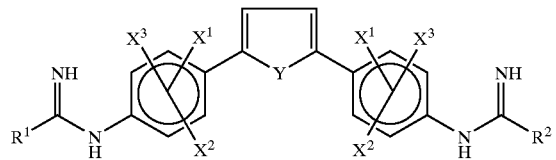

wherein Y is a heteroatom; $R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group; and instructions for use of the compound for the treatment of a subject having a disease or disorder associated with leishmaniasis.

DESCRIPTION OF THE DRAWINGS

This invention is further understood by reference to the drawings wherein.

Figure 1:
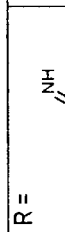
FIG. 1 provides a table of the data of the assays described herein for the reversed amidines tested.
Figure 1:
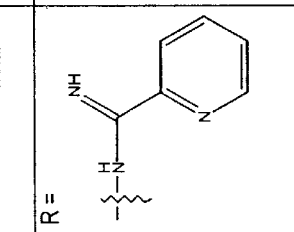
Figure 1:
Figure 1:
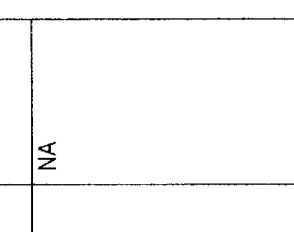

It is to be understood that both the foregoing general description and the following detailed description are exemplary and explanatory and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DETAILED DESCRIPTION OF THE INVENTION

Recently, dicationic 2,5-bis (4-guanidinophenyl) furans, 2,5-bis [4-(arylimino) aminophenyl]furans, and 2,5-bis [4-(alkylimino) aminophenyl]furans were synthesized starting from 2,5-bis [tri-n-butylstannyl]furan. These 2,5-bis {[alkyl (or aryl) imino]aminophenyl}furans are referred to herein as "reversed" amidines as the imino group of the amidine is attached to an "anilino" nitrogen in contrast to the original amidino furans wherein the imino group is directly attached to the aryl ring.

As described herein, these reversed amidines have been found to exhibit anti-leishmanial activity. In fact, the reversed amidines of the present invention are more effective than pentamidine against Leishmania. For example, when tested in vitro against macrophages infected with *L. mexicana*, pentamidine did not reduce the parasite burden as compared to untreated controls. However, as described herein, the reversed amidines of the present invention suppressed or inhibited *L. mexicana* infections in macrophages by about 50% at a concentration of about 0.1 µg/ml (for DB709 and DB710) to about 1.4 µg/ml (for DB667). Also, as described herein, the reversed amidines of the present invention suppressed or inhibited *L. donovani* infections in macrophages by about 50% at a concentration of about 0.1 µg/ml (for DB702) to about 1.4 µg/ml (for 1DWB667. In the *L. donovani* axenic amastigote assay, the reversed amidine compounds of the present invention suppressed or inhibited parasite growth by about 50% at a concentration of about 0.2 µg/ml (for DB702, DB709, and DB710) to about 10 µg/ml (for DB715 and DB716). Therefore, as described herein, the present invention provides reversed amidine compounds and methods of using for treating, preventing or inhibiting leishmaniasis.

As used herein, a "reversed amidine" compound refers to a compound having the following Structural Formula I:

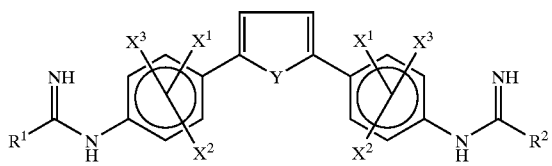

wherein Y is a heteroatom; $R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group.

Preferably, Y is O or S, $R^1$ and $R^2$ are independently H, phenyl, cyclohexyl, quinolyl, pyridinyl, or methylpyridinyl, and $X^1$, $X^2$, and $X^3$ are independently H, Cl, amino, methyl, methoxy, ethoxy, or propan-2-oxy.

Preferably, $X^1$, $X^2$, and $X^3$ are each independently at positions 2, 3, 5, or 6 of the phenyl rings, more preferably, $X^1$ and $X^2$ are each independently at positions 2 or 3.

FIG. 1 provides representative Structural Formulas of a few of the preferred compounds of the present invention.

The terms and abbreviations used in the instant disclosure have their normal meanings unless otherwise designated.

As used in the present application, the following definitions apply:

As used herein, diseases, disorders and infections "associated with" or "related to" leishmaniasis include those caused by leishmania parasites.

As used herein, "anti-leishmanial activity" refers to the activity of a compound which kills Leishmania parasites or prevents, inhibits, or suppresses leishmanial reproduction or proliferation.

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl group" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

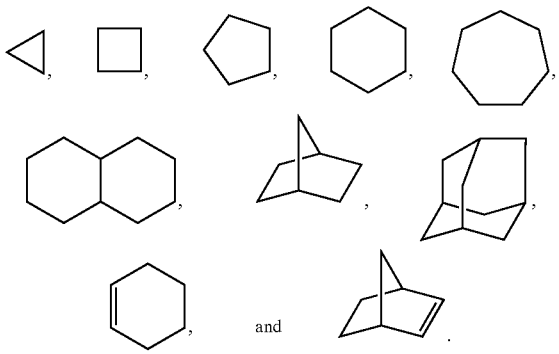

A "heterocycloalky group" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

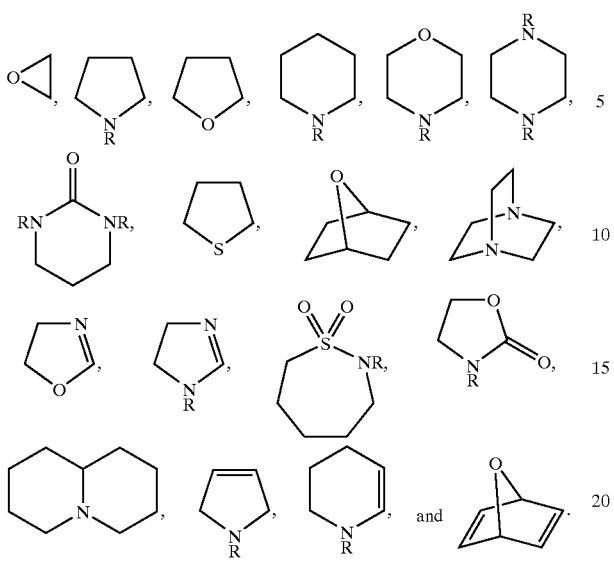

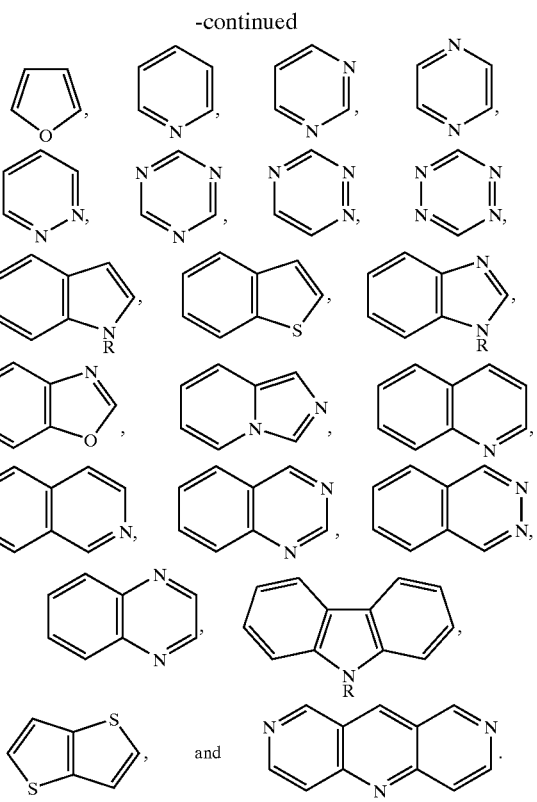

An "aryl group" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

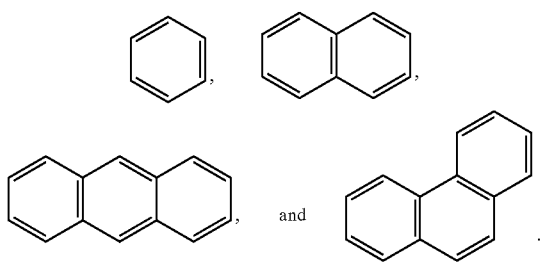

A "heteroaryl group" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

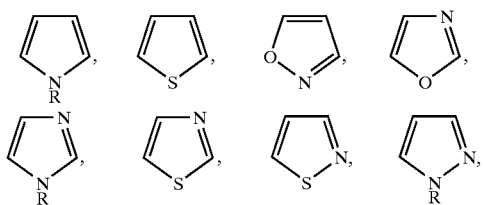

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl group" is intended to mean a —C(O)—$R_a$ radical, where $R_a$ is a suitable substituent as defined below.

A "thioacyl group" is intended to mean a —C(S)—$R_a$ radical, where $R_a$ is a suitable substituent as defined below.

A "sulfonyl group" is intended to mean a —SO$_2$$R_a$ radical, where $R_a$ is a suitable substituent as defined below.

A "hydroxy group" is intended to mean the radical —OH.

An "amino group" is intended to mean the radical —NH$_2$. A reversed amindine having an amino group as a substituent is commonly referred to as "guanidine".

An "alkylamino group" is intended to mean the radical —NHR$_a$, where R$_a$ is an alkyl group.

A "dialkylamino group" is intended to mean the radical —NR$_a$R$_b$, where R$_a$ and R$_b$ are each independently an alkyl group.

An "alkoxy group" is intended to mean the radical —OR$_a$, where R$_a$ is an alkyl group. Exemplary alkoxy groups include methoxy, ethoxy, propoxy, and the like.

An "alkoxycarbonyl group" is intended to mean the radical —C(O)OR$_a$, where R$_a$ is an alkyl group.

An "alkylsulfonyl group" is intended to mean the radical —SO$_2$R$_a$, where R$_a$ is an alkyl group.

An "alkylaminocarbonyl group" is intended to mean the radical —C(O)NHR$_a$, where R$_a$ is an alkyl group.

A "dialkylaminocarbonyl group" is intended to mean the radical —C(O)NR$_a$R$_b$, where R$_a$ and R$_b$ are each independently an alkyl group.

A "mercapto group" is intended to mean the radical —SH.

An "alkylthio group" is intended to mean the radical —SR$_a$, where R$_a$ is an alkyl group.

A "carboxy group" is intended to mean the radical —C(O)OH.

A "carbamoyl group" is intended to mean the radical —C(O)NH$_2$.

An "aryloxy group" is intended to mean the radical —OR$_c$, where R$_c$ is an aryl group.

A "heteroaryloxy group" is intended to mean the radical —OR$_d$, where R$_d$ is a heteroaryl group.

An "arylthio group" is intended to mean the radical —SR$_c$, where R$_c$ is an aryl group.

A "heteroarylthio group" is intended to mean the radical —SR$_d$, where R$_d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wutz, Protecting Groups in Organic Synthesis, 2$^{nd}$ edition, John Wiley and Sons, New York, N.Y. (1991).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); C$_{1-6}$-alkyl; C$_{1-6}$-alkenyl; C$_{1-6}$-alkynyl; hydroxyl; C$_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether; O-lower alkyl; O-aryl; aryl; aryl-lower alkyl; CO$_2$CH$_3$; CONH$_2$; OCH$_2$CONH$_2$; NH$_2$; SO$_2$NH$_2$; OCHF$_2$; CF$_3$; OCF$_3$; and the like. Such moieties may also be optionally substituted by a fused-ring structure or bridge, for example OCH$_2$—O. All of these substituents may optionally be further substituted with a substituent selected from groups such as hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a reversed amidine of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the reversed amidines may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the reversed amidines of the Structural Formula I, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

The reversed amidine compounds of the present invention may be prepared using reaction routes, synthesis schemes and techniques available in the art using starting materials that are readily available. The reversed amidine compounds of the present invention were made according to the following schemes and methods. However, it should be noted that the reversed amidine compounds of the present invention may be made other methods known in the art.

As illustrated by the following schemes, the reversed amidines 4 of the present invention may be synthesized from the corresponding diamino compounds 3.

As shown in Scheme 1, the diamino compounds 3 were prepared in two steps starting with a Stille coupling between 2,5-bis(tri-n-butylstannyl)furan 1 and a substituted 4-bromonitroarene to form the corresponding 2,5-bis (4-nitrophenyl) furans 2. This general reaction, as described in Kumar, A., et al. (1999) Heterocyclic Comm. 5:301–304, which is herein incorporated by reference, typically gave yields of about 65% to about 88% of the dinitro compounds.

Also, as in contrast to previously reported syntheses, the reaction allowed for the straightforward incorporation of substituents onto the two phenyl rings of the 2,5-diphenylfuran framework. See Bajic, M., et al. (1996) Heterocyclic Comm. 2:135, which is herein incorporated by reference.

Scheme 1:

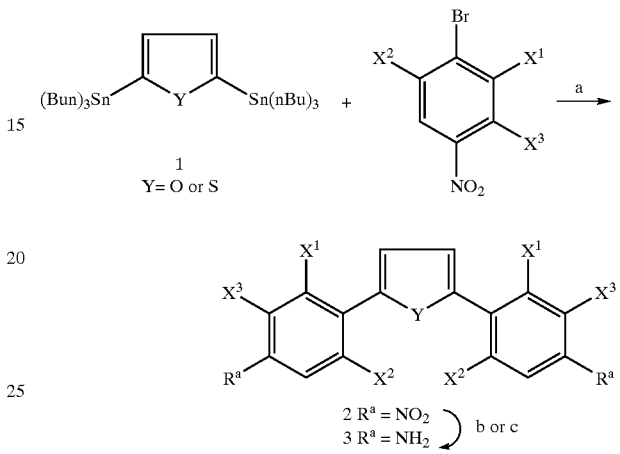

a) Pd(PPh$_3$)$_4$, 1,4-dioxane, Δ; b) H$_2$, Pd/C, EtOAc, EtOH; c) SnCl$_2$ dihydrate, EtOH, DMSO, Δ.

Legend for compounds 2–3:

| | |
|---|---|
| a X$^1$ = X$^2$ = X$^3$ = H, Y = O | h X$^1$ = O-2-Propyl, X$^2$ = X$^3$ = H, Y = O |
| b X$^1$ = Me, X$^2$ = X$^3$ = H, Y = O | i X$^1$ = X$^2$ = H, X$^3$ = OMe, Y = O |
| c X$^1$ = OMe, X$^2$ = X$^3$ = H, Y = O | j X$^1$ = X$^2$ = H, X$^3$ = OEt, Y = O |
| d X$^1$ = Cl, X$^2$ = X$^3$ = H, Y = O | k X$^1$ = Me, X$^2$ = X$^3$ = H, Y = S |
| e X$^1$ = CF$_3$, X$^2$ = X$^3$ = H, Y = O | 2l X$^1$ = OCH$_2$Ph, X$^2$ = X$^3$ = H, Y = O |
| f X$^1$ = Me, X$^2$ = Me, X$^3$ = H, Y = O | 3l X$^1$ = OH, X$^2$ = X$^3$ = H, Y = O |
| g X$^1$ = OEt, X$^2$ = X$^3$ = H, Y = O | |

Then, the 2,5-bis(4-nitrophenyl)furans 2 were reduced either by catalytic hydrogenation or by the action of stannous chloride, and generally produced the desired diamino compounds 3 in excellent overall yields. Specifically, the 2,5-bis(4-nitrophenyl)furans 2 were prepared by the following representative procedure, which is a modification of that described by Kumar, A. et al. (1999):

2,5-Bis(2-methyl-4-nitrophenyl)furan (2b) was prepared by adding 2,5-bis (tri-n-butylstannyl)furan (6.46 g, 10 mmol) to a solution of 2-bromo-5-nitrotoluene (4.32 g, 20 mmol) and tetrakis(triphenylphospine)palladium (0.40 g) in anhydrous 1,4-dioxane (50 ml). The mixture was heated overnight under nitrogen at about 95° C. to about 100° C. The resulting orange suspension was diluted with hexanes (15 ml), cooled to room-temperature, and filtered to give, after rinsing with hexanes, an orange solid (3.10 g), mp 241–243° C. The product was recrystallized from DMF (100 ml) to give a bright orange fluffy solid (2.87 g, 85%), mp 242–243° C. $^1$H NMR (DMSO-d$_6$): 2.69 (s, 6H), 7.31 (s, 2H), 8.12 (m, 4H), 8.23 (s, 2H). Anal. Calcd. for C$_{18}$H$_{14}$N$_2$O$_5$ (338.31): C, H, N.

2,5-Bis(4-nitrophenyl)furan (2a) was prepared according to the above representative procedure using 4-bromonitrobenzene as the bromonitroarene. Yield: 88%; orange fluffy solid; mp 269–270° C. lit. mp 270–272° C. See Ling, C. et al. (1994) J. Am. Chem. Soc. 116:8784–8792, which is herein incorporated by reference.

2,5-Bis(2-methoxy-4-nitrophenyl)furan (2c) was prepared according to the above representative procedure using 2-bromo-5-nitroanisole as the bromonitroarene. Yield: 77%; bright orange granular solid; mp 308–310° C. (DMF). $^1$H NMR (DMSO-$d_6$): 4.10 (s, 6H), 7.37 (s, 2H), 7.90 (s, 2H), 7.94 (d, 2H), 8.22 (d, 2H). Anal. Calcd. for $C_{18}H_{14}N_2O_7 \cdot 0.1H_2O$ (372.11): C, H, N.

2,5-Bis(2-chloro-4-nitrophenyl)furan (2d) was prepared according to the above representative procedure using 1-bromo-2-chloro-4-nitrobenzene as the bromonitroarene. Yield: 71%; fluffy orange solid; mp 247–247.5° C. (DMF/MeOH). $^1$H NMR (DMSO-$d_6$): 7.70 (s, 2H), 8.29 (dd, J=8.8, 2.2 Hz, 2H), 8.36 (d, J=8.8 Hz, 2H), 8.43 (d, J=2.2 Hz, 2H). Anal. Calcd. for $C_{16}H_8Cl_2N_2O_5$ (379.15): C, H, N.

2,5-Bis(4-nitro-2-trifluoromethylphenyl)furan (2e) was prepared according to the above representative procedure using 2-bromo-5-nitrobenzotrifluoride as the bromonitroarene. Yield: 74%; fluffy golden needles; mp 158.5–159° C. (EtOH). $^1$H NMR (DMSO-$d_6$): 7.38 (s, 2H), 8.24 (d, J=8.7 Hz, 2H), 8.57 (d, J=2.4 Hz, 2H), 8.62 (dd, J=8.6, 2.4 Hz, 2H). Anal. Calcd. for $C_{18}H_8F_6N_2O_5$ (446.26): C, H, N.

2,5-Bis(2,6-dimethyl-4-nitrophenyl)furan (2f) was prepared according to the above representative procedure using 2,6-dimethyl-4-nitrobromobenzene as the bromonitroarene. Yield: 65%; yellow needles; mp 156.5–157.5° C. (DMF/EtOH/$H_2O$). $^1$H NMR (DMSO-$d_6$): 2.34 (s, 12H), 6.85 (s, 2H), 8.04 (s, 4H). Anal. Calcd. for $C_{20}H_{18}N_2O_5$ (366.36): C, H, N.

2,5-Bis(2-ethoxy-4-nitrophenyl)furan (2 g) was prepared according to the above representative procedure using 2-ethoxy-4-nitrobromobenzene (mp 51–52.5° C., prepared by alkylation of 2-bromo-5-nitrophenol with iodoethane) as the bromonitroarene. Yield: 82%; red-orange crystalline solid; mp 272–272.5.5° C. (DMF). $^1$H NMR (DMSO-$d_6$): 1.50–1.52 (t, 6H), 4.37 (q, 4H), 7.40 (s, 2H), 7.87 (d, 2H), 7.93 (dd, 2H), 8.22 (d, 2H). Anal. Calcd. for $C_{20}H_{18}N_2O_7$ (398.36): C, H, N.

2,5-Bis[4-nitro-2-(2-propoxy)phenyl]furan (2 h) was prepared according to the above representative procedure using 2-(2-propoxy)-4-nitrobromobenzene (mp 41–43° C., prepared by alkylation of 2-bromo-5-nitrophenol with 2-iodopropane) as the bromonitroarene. Yield: 64%; orange fluffy needles; mp 253–254° C. (DMF/EtOH). $^1$H NMR (DMSO-$d_6$): 1.44 (d, 12H), 5.00 (m, 2H), 7.40 (s, 2H), 7.89 (d, 2H), 7.92 (dd, 2H), 8.22 (d, 2H).). Anal Calcd. for $C_{22}H_{22}N_2O_7$ (426.42): C, H, N.

2,5-Bis(3-methoxy-4-nitrophenyl)furan (2i) was prepared according to the above representative procedure using 3-methoxy-4-nitrobromobenzene (mp 90–91° C., prepared by reaction of 4-bromo-1,2-dinitrobenzene with NaOMe/MeOH. See Varenikova et al (1985) J. Org. Chem. USSR 21:1651, which is herein incorporated by reference) as the bromonitroarene. Yield: 77%; orange fluffy needles; mp 243–244° C. (DMF/MeOH). $^1$H NMR (DMSO-$d_6$): 4.05 (s, 6H), 7.52 (s, 2H), 7.62 (dd, 2H), 7.72 (d, 2H), 8.00 (d, 2H).

2,5-Bis(3-ethoxy-4-nitrophenyl)furan (2j) was prepared according to the above representative procedure using 3-ethoxy-4-nitrobromobenzene (mp 78–79° C., prepared by reaction of 4-bromo-1,2-dinitrobenzene with NaOEt/EtOH. See Varenikova et al.) as the bromonitroarene. Yield: 75%; yellow-orange fluffy solid; mp 192–194° C. (DMF/MeOH). $^1$H NMR (DMSO-$d_6$): 1.36–1.41 (t, 6H), 4.34 (t, 4H), 7.51 (s, 2H), 7.60 (dd, 2H), 7.69 (d, 2H), 7.97 (d, 2H).). Anal. Calcd. for $C_{20}H_{18}N_2O_7$ (398.36): C, H, N.

2,5-Bis(2-methyl-4-nitrophenyl)thiophene (2k) was prepared according to the above representative procedure using 2,5-(trimethylstannyl)thiophene (See Seitz, D. E. et al. (1983) Synth. Commun. 13:121, which is herein incorporated by reference) in place of the bis-stannylfuran and using 2-bromo-5-nitrotoluene as the bromonitroarene. Yield: 71%; orange micro-needles; mp 156–157° C. (DMF). $^1$H NMR (DMSO-$d_6$): 2.61(s, 6H), 7.55 (s, 2H), 7.78 (d, 2H), 8.11 (dd, 2H), 8.25 (d, 2H).

2,5-Bis(2-benzyloxy-4-nitrophenyl)furan (2l) was prepared according to the above representative procedure using 2-benzyloxy-4-nitrobromobenzene (See Amstutz (1950) J. Am. Chem. Soc. 72:3420, which is herein incorporated by reference) as the bromonitroarene. Yield: 75%; orange solid; mp 233–237° C. (DMF/EtOH). $^1$H NMR (DMSO-$d_6$): 5.45 (s, 4H), 7.24 (s, 2H), 7.38–7.45 (m, 6H), 7.53 (d, 4H), 7.92 (dd, 2H), 8.00 (dd, 2H), 8.18 (d, 2H).

To prepare the 2,5-bis(4-aminophenyl)furans 3a–c and 3e–j, and 3l, the following procedure was utilized:

2,5-Bis(4-amino-2-methylphenyl)furan (3b). To a suspension of the bis-nitro derivative 2b (2.87 g) in EtOAc (90 ml) and dry EtOH (10 ml) was added Pd/C (10%) (0.40 g) and the mixture was hydrogenated on a Parr apparatus at an initial pressure of about 50 psi. After the uptake of hydrogen subsided (generally 3–6 hours), the resulting solution was filtered over Celite and the pale yellow to colorless filtrate was concentrated in vacuo to near dryness to give, after dilution with hexanes, the pure diamine as a pale yellow/tan solid (2.17 g, 91%), mp 174–176° C., which required no purification. $^1$H NMR (DMSO-$d_6$): 2.33 (s, 6H), 5.15 (br s, 4H), 6.42 (s, 2H), 6.46 (m, 4H), 7.35 (d, 2H). MS (EI): m/z 278 ($M^+$).

2,5-Bis(4-aminophenyl)furan (3a) was prepared according to the above representative procedure using bis-nitro derivative 2a as starting material. Yield: 94%; pale yellow/tan solid; mp 218–221° C., lit[46] mp 213–216° C. MS (EI): m/z 250 ($M^+$).

2,5-Bis(4-amino-2-methoxyphenyl)furan (3c) was prepared according to the above representative procedure using bis-nitro derivative 2c as starting material. The resulting oil following evaporation of solvent was reconcentrated with benzene to give a yellow/tan solid which was triturated with ether. Yield: 79%; mp 201–202.5° C. $^1$H NMR (DMSO-$d_6$): 3.80 (s, 6H), 5.25 (br s, 4H), 6.24 (dd, J=8.3, 2.0 Hz, 2H), 6.30 (d, J=1.9 Hz 2H), 6.56 (s, 2H), 7.48 (d, J=8.4 Hz, 2H). MS (EI): m/z 310 ($M^+$).

2,5-Bis(4-amino-2-trifluoromethylphenyl)furan (3e) was prepared according to the above representative procedure using bis-nitro derivative 2e as starting material. The resulting red oil was crystallized from EtOAc/hexanes in two crops as a red/orange solid. Combined yield: 81%; mp (first/major crop) 89.5–91° C.; mp (second crop) 91.5–92° C. $^1$H NMR (DMSO-$d_6$): 5.79 (br s, 4H), 6.52 (s, 2H), 6.82 (dd, J=8.4, 2.4 Hz, 2H), 6.98 (d, J=2.2 Hz, 2H), 7.43 (d, J=8.4 Hz, 2H). MS (EI): m/z 386 ($M^+$).

2,5-Bis(4-amino-2,6-dimethylphenyl)furan (3f) was prepared according to the above representative procedure using bis-nitro derivative 2f as starting material. Yield: 99%; white fluffy solid; mp 144.5–146° C. $^1$ NMR (DMSO-$d_6$): 2.01 (s, 6H), 5.06 (br s, 4H), 6.24 (s, 2H), 6.29 (s, 4H). MS (EI): m/z 306 ($M^+$).

2,5-Bis(4-amino-2-ethoxyphenyl)furan (3 g) was prepared according to the above representative procedure using bis-nitro derivative 2 g as starting material. Yield: 98%; tan-rose solid (light sensitive), mp 192–193° C. $^1$H NMR (DMSO-$d_6$): 1.42 (t, 6H), 4.01 (q, 4H), 5.25 (br s, 4H), 6.23 (dd, 2H), 6.26 (d, 2H), 6.62 (s, 2H), 7.49 (d, 2H). MS (EI): m/z 338 (M$^+$).

2,5-Bis[4-amino-2-(2-propoxy)phenyl]furan (3 h) was prepared according to the above representative procedure using bis-nitro derivative 2 h as starting material. Yield: 99%; off-white solid. $^1$H NMR (DMSO-$d_6$): 1.33 (d, 12H), 4.56 (m, 2H), 5.20 (br s, 4H), 6.21 (dd, J=8.4, 1.8 Hz, 2H), 6.30 (d, J=1.8 Hz, 2H), 6.62 (s, 2H), 7.48 (d, J=8.4 Hz, 2H). MS (EI): m/z 366 (M$^+$).

2,5-Bis(4-amino-3-methoxyphenyl)furan (3i) was prepared according to the above representative procedure using bis-nitro derivative 2i as starting material. Yield: 70%; tan crystalline solid; mp 188–190° C. (MeOH). $^1$H NMR (DMSO-$d_6$): 3.84 (s, 6H), 4.88 (br s, 4H), 6.65–6.67 (m, 4H), 7.10–7.14 (m, 4H). MS (EI): m/z 310 (M$^+$).

2,5-Bis(4-amino-3-ethoxyphenyl)furan (3j) was prepared according to the above representative procedure using bis-nitro derivative 2j as starting material. Yield: 85%; tan-green solid. $^1$H NMR (DMSO-$d_6$): 1.37 (t, 6H), 4.07 (q, 4H), 4.85 (br s, 4H), 6.63 (s, 2H), 6.65 (d, 2H), 7.08–7.12 (m, 4H). MS (EI): m/z 338 (M$^+$).

2,5-Bis(4-amino-2-hydroxyphenyl)furan (3l) was prepared according to the above representative procedure using the benzyloxy-substituted bis-nitro derivative 2l as starting material. Yield: 100%; light brown solid. $^1$H NMR (DMSO-$d_6$): 5.09 (br s, 4H), 6.10–6.15 (m, 4H), 6.58 (s, 2H), 7.39 (d, 2H), 9.46 (s, 2H).

To prepare the 2,5-bis(4-aminophenyl)furans 3d and 3k, the following procedure was utilized:

2,5-Bis(4-amino-2-chlorophenyl)furan (3d). To a suspension of the corresponding bis-nitro derivative 2d (1.22 g, 3.2 mmol) in dry EtOH (100 ml) and DMSO (20 ml) was added SnCl$_2$.2H$_2$O (5.80 g, 25.7 mmol) and the mixture was heated under nitrogen at 80° C. After about 4 to about 5 hours, TLC showed that starting material had been consumed, and thus the mixture was cooled, neutralized with NaOH (aq), and extracted with EtOAc. The extract was washed with water, brine, then dried (Na$_2$SO$_4$) and concentrated. The resulting oil was crystallized from benzene/hexane with partial concentration to give a light brown solid (0.74 g, 71%), mp 191.5–193° C. Catalytic hydrogenation was not explored. $^1$H NMR (DMSO-$d_6$): 5.60 (br s, 4H), 6.61 (dd, J=8.6, 2.2 Hz, 2H), 6.68 (d, J=2.2 Hz 2H), 6.82 (s, 2H), 7.56 (d, J=8.6 Hz, 2H). MS (EI): m/z 318 (M$^+$).

2,5-Bis(4-amino-2-methylphenyl)thiophene (3k) was prepared according to the above representative procedure using bis-nitro derivative 2k as starting material. Yield: 89%; yellow micro-needles, mp 86–88° C. (ethyl ether/hexanes). $^1$H NMR (DMSO-$d_6$): 2.28 (s, 6H), 5.15 (br s, 4H), 6.42 (dd, J=8.0, 1.8 Hz, 2H), 6.47 (d, J=1.8 Hz, 2H), 6.89 (s, 2H), 7.06 (d, J=8.0 Hz, 2H).

As shown in Scheme 2, the first of the reversed amidines (4b) was prepared from the corresponding diamide via a two-step process which involved conversion of the latter to the diimidoyl chloride using SOCl$_2$, followed by reaction with anhydrous ammonia. See Boykin, D. W., et al. (1995) J. Med. Chem. 38:912–916, which is herein incorporated by reference.

Scheme 2:

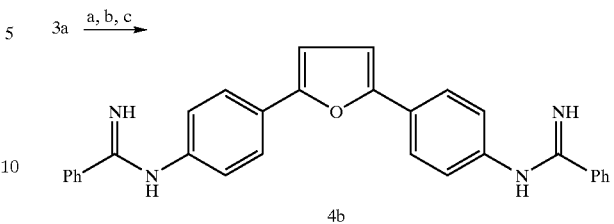

a) PhCOCl, TEA, MeCN; b) SOCl$_2$, DMF, CH$_2$Cl$_2$, Δ; c) NH$_3$, EtOH.

2,5-Bis[4-(benzimidoylamino)phenyl]furan Dihydrochloride (4b, DB613).

To a chilled solution of 2,5-bis(4-aminophenyl)furan (0.25 g, 1.0 mmol) in dry acetonitrile (10 ml) was added triethylamine (0.22 g, 2.1 mmol) followed dropwise by benzoyl chloride (0.30 g, 2.1 mmol) and the resulting suspension was stirred at room-temperature for 3 hours. Water (10 ml) was then added and the precipitate was collected, rinsed with water, followed by MeOH, and finally dried in vacuo to give 2,5-bis(4-benzamidophenyl)furan as a tan solid (0.44 g, 96%), mp 312–314.5° C. $^1$H NMR (DMSO-$d_6$): 6.98 (s, 2H), 7.52–7.62 (m, 6H), 7.80 (d, 4H), 7.89 (d, 4H), 7.97 (d, 4H), 10.33 (br s, 2H).

The intermediate bis(benzamide) (0.44 g, 0.96 mmol) was suspended in anhydrous dichloromethane (40 ml) and treated with freshly distilled thionyl chloride (0.68 g, 5.7 mmol) along with 2 drops of DMF and the mixture was refluxed with vigorous stirring until a solution was obtained (20 hours). The solution was then concentrated in vacuo to give a yellow solid, which was co-evaporated with dry benzene. The obtained imidoyl chloride was dissolved in anhydrous dichloromethane (40 ml) and the solution was saturated at ice/water-bath temperature with anhydrous ammonia and sealed. After stirring overnight at room-temperature, the turbid mixture was concentrated to give a yellow solid, which was triturated with 0.5N NaOH, collected, and air dried. This free-base (0.44 g, 100%) was dissolved in boiling EtOH (50 ml), filtered, and at ice-bath temperature was treated with dry HCl. After dilution with ether, the solution was concentrated (high vacuum) to give the dihydrochloride as an orange hygroscopic solid, mp 242–248° C. $^1$H NMR (DMSO-$d_6$): 7.26 (s, 2H), 7.58 (d, 4H), 7.67 (t, 4H), 7.78 (t, 2H), 7.95 (d, 4H), 8.03 (d, 4H), 9.12 (br s, 2H), 9.94 (br s, 2H), 11.66 (br s, 2H). MS (EI): m/z 456 (M$^+$, 100), 353 (63), 250 (62), 221 (16), 130 (15), 103 (41), 76 (14), 44 (22). Anal. Calcd. for C$_{30}$H$_{24}$N$_4$O.2HCl.0.5H$_2$O.0.1(C$_2$H$_5$)$_2$O (545.87): C, H, N.

Alternatively, the remainder of the diamidines 4 were prepared by reacting the diamines 3 with two equivalents of a non-odoriferous S-(2-naphthylmethyl)thioimidate in EtOH/MeCN as shown in Scheme 3. See Shearer, B. G., et al. (1997) Tetrahedron Lett. 38:179–182 and Collins, J. L., et al. (1998) J. Med. Chem. 41:2858–2871, and Stephens, C. E., et al (2000) J. Med. Chem. 44:1741–1748, which are herein incorporated by reference.

Scheme 3:

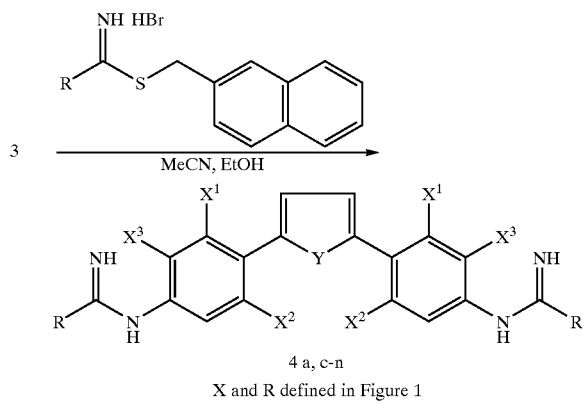

4 a, c-n

X and R defined in Figure 1

This reaction gave yields of about 60% to about 80% when the diamine was unsubstituted or substituted with electron-donating groups; however, when the diamine was substituted with the deactivating chloro group, the yield was reduced by about 25%, and with the strongly deactivating trifluoromethyl group, the diamidine could not be isolated.

Alternative preparation of bis-{[alkyl(or aryl)imino] aminophenyl}furan derivatives 4 (Scheme 3). The following experimental is representative. In some cases, the free base was purified by recrystallization as indicated.

2,5-Bis[2-methyl-4-(2-pyridylimino)aminophenyl]furan (4f, DB702). To a solution of 2,5-bis(4-amino-2-methylphenyl)furan (0.30 g, 1.08 mmol) in dry MeCN (5 ml) was added dry EtOH (15 ml) and the solution was chilled briefly on an ice/water bath. S-(2-Naphthylmethyl)-2-pyridylthioimidate hydrobromide (0.815 g, 2.27 mmol) was then added and the mixture was stirred overnight at room-temperature. The resulting solution was concentrated to an oil, which was triturated with ether to give a yellow solid. The solid was collected, dissolved in EtOH and basified with NaOH (1N), and the free base was extracted into EtOAc. After drying ($Na_2SO_4$) and partially concentrating, the resulting suspension was diluted with ether to give a fluffy yellow solid (0.36 g, 69%), mp 188–189° C., which required no purification. $^1$H NMR (DMSO-$d_6$): 2.51 (s, 6H), 6.60 (br s, 4NH), 6.77 (s, 2H), 6.87 (m, 4H), 7.55 (dd, 2H), 7.74 (d, 2H), 7.95 (m, 2H), 8.31 (d, 2H), 8.63 (d, 2H).

To prepare the hydrochloride salt, the free base was suspended in EtOH (40 ml) and treated with dry HCl gas for about 5 to about 10 minutes at ice-bath temperature. The resulting solution was then concentrated in vacuo to near dryness to give an orange suspension which was diluted with ether (40 ml) and filtered to yield an orange powder (0.40 g), mp>180° C. dec. $^1$H NMR (DMSO-$d_6$): 2.62 (s, 6H), 7.08 (s, 2H), 7.44 (d, 2H), 7.47 (s, 2H), 7.85 (dd, 2H), 7.99 (d, 2H), 8.22 (t, 2H), 8.49 (d, 2H), 8.89 (d, 2H), 9.36 (br s, 2H), 10.13 (br s, 2H), 11.88 (br s, 2H). MS (EI): m/z 486 ($M^+$, 100), 382 (77.9), 278 (12.8), 104 (20.0), 78 (8.8), 43 (28.9). Anal. Calcd. for $C_{30}H_{26}N_6O.3.5HCl.0.5H_2O$ (623.20): C, H, N, Cl.

2,5-Bis[4-(2-pyridylimino)aminophenyl]furan (4a, DB667, or 1DWB667) was prepared according to the procedure for 4f using diamine 3a and S-(2-naphthylmethyl)-2-pyridylthioimidate hydrobromide as starting materials. Free base: yellow crystalline solid, mp 221–223° C. (DMF/EtOH/$H_2O$). Yield: 65% $^1$H NMR (DMSO-$d_6$): 6.80 (br s, 4NH), 6.94 (s, 2H), 7.03 (d, 4H), 7.56 (m, 2H), 7.77 (d, 4H), 7.96 (m, 2H), 8.32 (d, 2H), 8.64 (m, 2H). Hydrochloride: Orange powder, mp>175° C. dec. $^1$H NMR (DMSO-$d_6$): 7.26 (s, 2H), 7.58 (d, 4H), 7.85 (dd, 2H), 8.03 (d, 4H), 8.22 (t, 2H), 8.52 (d, 2H), 8.89 (d, 2H), 9.39 (br s, 2H), 10.16 (br s, 2H), 11.91 (br s, 2H). MS (EI): m/z 458 ($M^+$, 100), 354 (49.1), 250 (27.6), 221 (8.9), 130 (9.4), 105 (13.6), 78 (8.6). Anal. Calcd. for $C_{28}H_{22}N_6O.3.5HCl$ (586.12): C, H, N, Cl.

2,5-Bis[4-(cyclohexylimino)aminophenyl]furan (4c, DB656) was prepared according to the procedure for 4f using diamine 3a and S-(2-naphthylmethyl)-cyclohexanethioimidate hydrobromide as starting materials. Free base: pale yellow needles, mp 242–243° C. dec (EtOAc). Yield: 17%. $^1$H NMR (DMSO-$d_6$): 1.18–1.90 (m, 20H), 2.14 (m, 2H), 5.71 (br s, 4NH), 6.82 (s, 2H), 7.63 (d, 4H). In addition, a 41% yield of the mono-amidine/mono-amine (free base: yellow solid, mp 195–196° C.) was isolated by chromatography on silica (EtOAc-MeOH, 9:1). The insoluble nature of the reaction medium was the likely cause of the incomplete reaction. Dihydrochloride: tan/peach solid, mp 244–248° C. dec. $^1$H NMR (DMSO-$d_6$): 1.27 (m, 6H), 1.63–1.96 (m, 14H), 2.72 (m, 2H), 7.22 (s, 2H), 7.40 (d, 4H), 7.96 (d, 2H), 8.60 (br s, 2H), 9.34 (br s, 2H), 11.39 (br s, 2H). MS (FAB, thioglycerol): m/z 469.4 ($MH^+$, 100). Anal. Calcd. for $C_{30}H_{38}N_4O.2HCl.0.75EtOH.0.25H_2O$ (580.60): C, H, N.

2,5-Bis[4-(acetimidoyl)aminophenyl]furan Dihydrobromide (4d, DB611) was prepared according to the procedure for 4f using diamine 3a and S-(2-naphthylmethyl) thioacetimidate hydrobromide as starting materials. This compound was purified and characterized as the HBr salt without conversion to the free base. Fluffy tan/orange solid, mp 307–309.5° C. dec (MeOH/EtOAc). Yield: 57%. $^1$H NMR (DMSO-$d_6$, 70° C.): 2.37 (s, 6H), 7.17 (s, 2H), 7.40 (d, 4H), 7.94 (d, 4H), 8.52 (br, s 2H), 9.43 (br s, 2H), 11.13 (br s, 2H). MS (FAB, thioglycerol): m/z 333.2 ($MH^+$, 100). Anal. Calcd. for $C_{20}H_{20}N_4O.2.0HBr$ (494.23): C, H, N.

2,5-Bis[4-(benzimidoyl)amino-2-methylphenyl]furan (4e, DB626) was prepared according to the procedure for 4f using diamine 3b and S-(2-naphthylmethyl)-thiobezimidate hydrobromide as starting materials. Free base: yellow crystalline solid. Yield: 60%. $^1$H NMR (DMSO-$d_6$): 2.48 (s, 6H), 6.50 (br s, 4NH), 6.75 (s, 2H), 6.84 (s, 4H), 7.44 (m, 6H), 7.71 (d, 2H), 7.95 (d, 4H). Hydrochloride: orange/yellow hygroscopic solid. $^1$H NMR (DMSO-$d_6$): 2.61 (s, 6H), 7.03 (s, 2H), 7.38–7.44 (m, 4H), 7.63–7.68 (m, 4H), 7.75–7.80 (m, 2H), 7.94 (d, 6H). MS (EI): m/z 484 ($M^+$, 100), 3.81 (87.2), 278 (37.9), 235 (5.4), 218 (3.1), 190 (5.5), 144 (11.1), 103 (32.8), 76 (9.3). Anal. Calcd. for $C_{32}H_{28}N_4O.2HCl.0.66H_2O$ (569.39): C, H, N.

2,5-Bis[2-methyl-4-(2-quinolylimino)aminophenyl]furan (4 g, DB716) was prepared according to the procedure for 4f using diamine 3b and S-(2-naphthylmethyl)-2-quinolylthioimidate hydrobromide as starting materials. Free base: orange powdery crystals, mp 168–169° C. (EtOH). Yield: 52%. $^1$H NMR (DMSO-$d_6$): 2.54 (s, 6H), 6.80 (s, 2H), 6.95 (m, 4H), 7.69 (m, 2H), 7.78 (d, 2H), 7.84 (m, 2H), 8.07 (d, 2H), 8.12 (d, 2H), 8.44 (d, 2H), 8.50 (d, 2H). Dihydrochloride: orange solid, mp>185° C. dec. $^1$H NMR (DMSO-$d_6$): 2.65 (s, 6H), 7.10 (s, 2H), 7.50 (m, 4H), 7.85 (m, 2H), 8.01 (m, 2H), 8.20 (d, 2H), 8.26 (d, 2H), 8.46 (d, 2H), 8.80 (d, 2H), 9.44 (br s, 2H), 10.21 (br s, 2H), 11.98 (br s, 2H). MS (FAB, thioglycerol): m/z 587.2 ($MH^+$, 100). Anal. Calcd. for $C_{38}H_{30}N_6O.2.0HCl.1.75H_2O$ (691.13): C, H, N, Cl.

2,5-Bis[2-methyl-4-(5-methyl-2-pyridylimino) aminophenyl]furan (4 h, DB710) was prepared according to the procedure for 4f using diamine 3b and S-(2-naphthylmethyl)-5-methyl-2-pyridylthioimidate hydrobromide as starting materials. Free base: yellow crystalline solid, mp 156–158° C. (Et$_2$O/hexanes). Yield: 74%. $^1$H NMR (DMSO-d$_6$): 2.37 (s, 6H), 2.50 (s, 6H), 6.55 (br s, 4NH), 6.75 (s, 2H), 6.85 (m, 4H), 7.70–7.76 (m, 4H), 8.18 (d, 2H), 8.45 (s, 2H). Hydrochloride: orange solid, mp>175° C. dec. $^1$H NMR (DMSO-d$_6$): 2.49 (s, 6H), 2.62 (s, 6H), 7.08 (s, 2H), 7.43 (d, 2H), 7.47 (s, 2H), 7.85 (dd, 2H), 7.98 (d, 2H), 8.03 (d, 2H), 8.42 (d, 2H), 8.74 (s, 2H), 9.29 (br s, 2H), 10.07 (br s, 2H), 11.83 (br s, 2H). MS (EI): m/z 514 (M$^+$, 19.2), 396 (100), 278 (34.5), 144 (8.0), 118 (33.6), 91 (13.6), 43 (22.8). Anal. Calcd. for C$_{32}$H$_{30}$N$_6$O.3.25HCl.0.75H$_2$O (646.62): C, H, N, Cl.

2,5-Bis[2-methoxy-4-(2-pyridylimino)aminophenyl]furan (4I, DB709) was prepared according to the procedure for 4f using diamine 3c and S-(2-naphthylmethyl)-2-pyridylthioimidate hydrobromide as starting materials. Free base: Bright yellow crystalline solid, mp 196–197° C. (EtOAc/Et$_2$O). Yield: 75%. $^1$H NMR (DMSO-d$_6$): 3.92 (s, 6H), 6.64 and 6.67 (d, 2H and s, 2H, overlapping a broad NH signal), 6.89 (s, 2H), 7.55 (dd, 2H), 7.86 (d, 2H), 7.95 (m, 2H), 8.32 (d, 2H), 8.63 (d, 2H). Dihydrochloride: brick orange solid, mp >180° C. dec. $^1$H NMR (DMSO-d$_6$): 4.00 (s, 6H), 7.16 (s, 2H), 7.18 (d, 2H), 7.34 (s, 2H), 7.85 (dd, 2H), 8.13 (d, 2H), 8.22 (t, 2H), 8.49 (d, 2H), 8.89 (d, 2H), 9.39 (br s, 2H), 10.15 (br s, 2H), 11.89 (br s, 2H), MS (EI): m/z 518 (M$^+$, 100), 414 (90.0), 371 (13.3), 310 (12.7), 267 (9.7), 155 (6.02), 104 (25.9), 77 (9.6), 43 (13.6). Anal Calcd. for C$_{30}$H$_{26}$N$_6$O.2.0HCl.2.0H$_2$O (627.51): C, H, N, Cl.

2,5-Bis[2-chloro-4-(2-pyridylimino)aminophenyl]furan (4j, DB712) was prepared according to the procedure for 4f using diamine 3d and S-(2-naphthylmethyl)2-pyridylthioimidate hydrobromide as starting materials. Free base: orange crystalline solid, mp 189–190° C. (EtOH). Yield: 25%. $^1$H NMR (DMSO-d$_6$): 6.85 (br s, 4NH), 7.02 (dd, 2H), 7.08 (d, 2H), 7.17 (s, 2H), 7.56 (m, 2H), 7.93–7.98 (m, 4H), 8.29 (d, 2H), 8.64 (m, 2H). Dihydrochloride: yellow/orange solid, mp>180° C. dec. $^1$H NMR (DMSO-d$_6$): 7.45 (s, 2H), 7.60 (d, 2H), 7.80 (s, 2H), 7.86 (dd, 2H), 8.23 (m, 4H), 8.50 (d, 2H), 8.90 (d, 2H), 9.54 (br s, 2H), 10.23 (br s, 2H), 11.98 (br s, 2H). MS (EI): m/z 530, 528, 526 (M$^+$, 13.2, 69.8, 100), 426, 424, 422 (7.9, 48, 72.4), 322, 320, 318 (2.6, 17.4, 26.6). Anal. Calcd. for C$_{28}$H$_{20}$Cl$_2$N$_6$O.2.0HCl.1.5H$_2$O (627.35): C, H, N, Cl.

2,5-Bis[2,6-dimethyl-4-(2-pyridylimino)aminophenyl]furan (4k, DB714) was prepared according to the procedure for 4f using diamine 3f and S-(2-naphthylmethyl)-2-pyridylthioimidate hydrobromide as starting materials. Free base: pale yellow crystals, mp 206–207° C. (EtOH). Yield: 80%. $^1$H NMR (DMSO-d$_6$): 2.19 (s, 12H), 6.47 (s, 2H), 6.55 (br s, 4NH), 6.69 (s, 4H), 7.54 (m, 2H), 7.94 (m, 2H), 8.29 (d, 2H), 8.62 (d, 2H). Hydrochloride: fluffy yellow solid. $^1$H NMR (DMSO-d$_6$): 2.28 (s, 12H), 6.68 (s, 2H), 7.28 (s, 4H), 7.84 (m, 2H), 8.21 (t, 2H), 8.48 (d, 2H), 8.88 (d, 2H), 9.37 (br s, 2H), 10.12 (br s, 2H), 11.87 (br s, 2H). MS (EI): m/z 514 (M$^+$, 8.5), 410 (38.7), 306 (100), 291 (16.0), 148 (45.4), 104 (56.3). Anal. Calcd. for C$_{32}$H$_{30}$N$_6$O.3.75HCl.0.5H$_2$O (660.35): C, H, N, Cl.

2,5-Bis [2-(2-propoxy)-4-(2-pyridylimino)aminophenyl]furan (4l, DB766) was prepared according to the procedure for 4f using diamine 3 h and S-(2-naphthylmethyl)-2-pyridylthioimidate hydrobromide as starting materials. Free base: yellow oil obtained by extraction with EtOAc. The oil failed to crystallize from EtOH/H$_2$O and was thus converted to the dihydrochloride directly. Dihydrochloride: brick orange hygroscopic solid. $^1$H NMR (DMSO-d$_6$): 1.43 (d, 12H), 4.83 (m, 2H), 7.14 (d, 2H), 7.18 (s, 2H), 7.31 (s, 2H) 7.85 (dd, 2H), 8.13 (d, 2H), 8.22 (t, 2H), 8.49 (d, 2H), 8.89 (d, 2H), 9.25 (br s, 2H), 10.01 (br s, 2H), 11.85 (br s, 2H). MS (EI): m/z 574 (M$^+$, 100), 470 (72.5). Anal. Calcd. for C$_{34}$H$_{34}$N$_6$O$_3$.2.1HCl.1.0H$_2$O (669.25): C, H, N, Cl.

2,5-Bis[2-(2-propoxy)-4-(5-methyl-2-pyridylimino)aminophenyl]furan (4m, DB786) was prepared according to the procedure for 4f using diamine 3 h and S-(2-naphthylmethyl)-5-methyl-2-pyridylthioimidate hydrobromide as starting materials. Free base: yellow solid. Yield: 70%. Dihydrochloride: orange hygroscopic solid, mp 185–194° C. $^1$H NMR (DMSO-d$_6$): 1.43 (d, 12H), 4.84 (m, 2H), 7.14 (d, 2H), 7.19 (s, 2H), 7.30 (s, 2H) 8.03 (d, 2H), 8.13 (d, 2H), 8.38 (d, 2H), 8.75 (s, 2H), 9.23 (br s, 2H), 10.02 (br s, 2H), 11.78 (br s, 2H). MS (CI): m/z 603 (MH$^+$, 39), 485 (52), 366 (69), 119(100). Anal. Calcd. for C$_{36}$H$_{38}$N$_6$O$_3$.2.0HCl.1.5H$_2$O (702.66): C, H, N, Cl.

2,5-Bis[3-ethoxy-4-(2-pyridylimino)aminophenyl]furan (4n, DB785) was prepared according to the procedure for 4f using diamine 3j and S-(2-naphthylmethyl)-2-pyridylthioimidate hydrobromide as starting materials. Free base: golden crystalline solid (EtOH/H$_2$O, then EtOH) Yield: 35%. $^1$H NMR (DMSO-d$_6$): 1.26 (t, 6H), 4.10 (q, 4H), 6.42 (br s, 4NH), 6.92 (d, 2H), 6.96 (s, 2H), 7.35 (m, 4H), 7.54 (m, 2H), 7.95 (m, 2H), 8.32 (d, 2H), 8.62 (m, 2H). Dihydrochloride: yellow/orange hygroscopic solid, mp 205–210° C. $^1$H NMR (DMSO-d$_6$): 1.33 (t, 6H), 4.27 (q, 2H), 7.34 (s, 2H), 7.47 (d, 2H), 7.60 (m, 4H) 7.85 (m, 2H), 8.21 (t, 2H), 8.47 (d, 2H), 8.89 (d, 2H), 9.08 (br s, 2H), 10.10 (br s, 2H), 11.56 (br s, 2H). MS (CI): m/z 547 (MH$^+$, 100), 107 (46). Anal. Calcd. for C$_{32}$H$_{30}$N$_6$O$_3$.2.0HCl.2.0H$_2$O (655.56): C, H, N, Cl.

2,5-Bis[3-methoxy-4-(2-pyridylimino)aminophenyl]furan (4o, DB746) was prepared according to the procedure for 4f using diamine 3i and S-(2-naphthylmethyl)-2-pyridylthioimidate hydrobromide as starting materials. Free base: yellow crystalline solid, mp 212–213° C. (DMF/H$_2$O). Yield: 70%. $^1$H NMR (DMSO-d$_6$): 3.82 (s, 6H), 6.89 (d, 2H), 6.98 (s, 2H), 7.38 (m, 4H), 7.54 (dd, 2H), 7.95 (dd, 2H), 8.32 (d, 2H), 8.62 (d, 2H). Dihydrochloride: yellow solid. $^1$H NMR (DMSO-d$_6$): 3.97 (s, 6H), 7.36 (s, 2H), 7.47 (d, 2H), 7.62 (d, 4H), 7.85 (dd, 2H), 8.20 (d, 2H), 8.45 (d, 2H), 8.89 (d, 2H), 9.37 (br s, 2H), 10.10 (br s, 2H), 11.86 (br s, 2H). Anal. Calcd. for C$_{30}$H$_{26}$N$_6$O.2.0HCl.1.0H$_2$O (609.5): C, H, N, Cl.

2,5-Bis[2-hydroxy-4-(2-pyridylimino)aminophenyl]furan (4p, DB750) was prepared according to the procedure for 4f using diamine 3l and S-(2-naphthylmethyl)-2-pyridylthioimidate hydrobromide as starting materials. Free base: yellow crystalline solid, mp 163.5–165° C. (EtOH/H$_2$O). Yield: 69%. $^1$H NMR (DMSO-d$_6$): 6.49–6.55 (m, 6H), 6.91 (s, 2H), 7.53–7.56 (m, 2H), 7.77 (d, 2H), 7.92–7.96 (m, 2H), 8.29 (d, 2H), 8.62 (d, 2H), 9.95 (br s, 2H). Dihydrochloride: orange solid. $^1$H NMR (DMSO-d$_6$): 7.02 (d, 2H), 7.14 (s, 2H), 7.16 (s, 2H), 7.82–7.85 (m, 2H), 8.03 (d, 2H), 8.20 (t, 2H), 8.43 (d, 2H), 8.88 (d, 2H), 9.30 (br s, 2H), 10.04 (br s, 2H), 10.94 (s, 2H), 11.76 (br s, 2H). Anal. Calcd. for C$_{28}$H$_{22}$N$_6$O$_3$.2.0HCl.1.5H$_2$O (590.46): C, H, N, Cl.

As shown in Scheme 4, the guanidines 6 were prepared by reaction of the diamines 3 with 1,3-Bis(tert-butoxycarbonyl)-2-methyl-2-thiopseudourea in the presence of mercury(II) chloride and triethylalmine to give the intermediate Boc-protected guanidines 5. The protected guanidines 5 were then subsequently deprotected by reaction with anhydrous HCl in EtOH/CH$_2$Cl$_2$ to give the guanidine hydrochlorides 6 directly. See W. Su, Synth. Comm. (1996) 26:407–413, which is herein incorporated by reference.

Scheme 4:

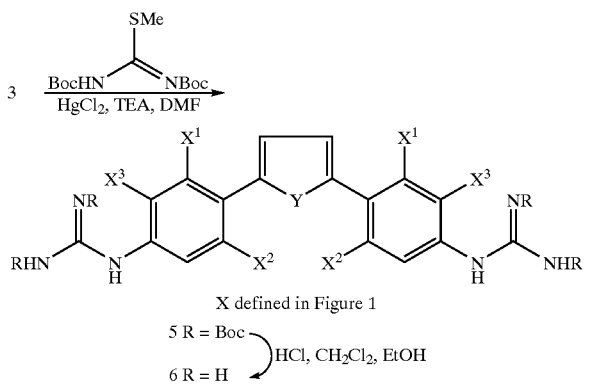

5 R = Boc
6 R = H  } HCl, CH$_2$Cl$_2$, EtOH

Preparation of 2,5-bis(guanidinophenyl)furan derivatives 6 (Scheme 4). The following procedure is representative:

2,5-Bis(2-ethoxy-4-guanidinophenyl)furan (6a, DB762). To a slightly chilled solution of diamine 3 g (0.27 g, 0.8 mmol), 1,3-Bis(tert-butoxycarbonyl)-2-methyl-2-thiopseudourea (0,496 g, 1.7 mmol) and dry triethylamine (0.512 g, 5 mmol) in anhyudrous dimethylformamide (DMF) was added mercury(II) chloride (0.504 g, 1.86 mmol) and the resulting suspension was stirred under nitrogen and at room-temperature overnight (about 16 to about 20 hr). The suspension was then diluted with CH$_2$Cl$_2$ and aqueous Na$_2$CO$_3$ solution and filtered over Celite to remove inorganic salts. The organic phase was separated and washed several times with water, then with brine, and finally dried (Na$_2$SO$_4$). Removal of the solvent gave an oil which was crystallized by addition of MeOH to yield a yellow solid. Reprecipitation of the collected product from CH$_2$Cl$_2$/MeOH (with partial concentration) gave the pure Boc-protected guanidine as a yellow solid. Yield: 78%. $^1$H NMR (CDCl$_3$): 1.50–1.55 (2s and t, 42H), 4.17 (q, 4H), 7.01 (s, 2H), 7.12 (d, 2H), 7.55 (s, 2H) 7.87 (d, 2H), 10.34 (s, 2H), 11.54 (br s, 2H). For deprotection, the boc-protected guanidine was dissolved in CH$_2$Cl$_2$ and then diluted with EtOH. This solution was then saturated with anhydrous HCl gas and stirred for about 2 to about 3 days at room temperature. Removal of solvent in vacuo gave the guanidine hydrochloride directly as a tan hygroscopic solid in quantitative yield. $^1$H NMR (DMSO-d$_6$): 1.47 (t, 6H), 4.21 (q, 4H), 6.89–6.97 (m, 4H), 7.06 (s, 2H), 7.58 (br s, NHs), 7.96 (dd, 2H), 10.09 (br s, 2H). MS (FAB, thioglycerol): m/z 423 (MH$^+$). Anal. Calcd. for C$_{22}$H$_{26}$N$_6$O$_3$·2.0HCl.1.25H$_2$O (517.92): C, H, N.

2,5-Bis[4-guanidino-2-(2-propoxy)phenyl]furan (6b, DB778) was prepared according to the procedure for 6a using diamine 3 h as starting material. Bis-Boc derivative: light orange solid. Yield: 76%. $^1$H NMR (CDCl$_3$): 1.45–1.55 (2s and d, 48H), 4.69 (m, 2H), 6.94 (dd, 2H), 7.01 (s, 2H), 7.73 (s, 2H) 7.85 (d, 2H), 10.30 (s, 2H), 11.51 (br s, 2H). Dihydrochloride: light brown hygroscopic solid. $^1$H NMR (DMSO-d$_6$): 1.38 (d, 12H), 4.79 (m, 2H), 6.87 (d, 2H), 6.97 (d, 2H), 7.06 (s, 2H), 7.58 (br s, NHs), 7.95 (dd, 2H), 10.06 (br s, 2H). MS (ES): m/z 451 (MH$^+$). Anal. Calcd. for C$_{24}$H$_{30}$N$_6$O$_3$·2.0HCl.1.25H$_2$O (545.97): C, H, N.

2,5-Bis(4-guanidino-3-methoxyphenyl)furan (6c, DB763) was prepared according to the procedure for 6a using diamine 3i as starting material. Bis-Boc derivative: yellow/tan solid. Yield: 70%. $^1$H NMR (CDCl$_3$): 1.51–1.53 (2s, 36), 3.99 (s, 6H), 6.66 (s, 2H), 7.20 (s, 2H), 7.37 (d, 2H) 8.55 (d, 2H), 10.77 (s, 2H), 11.59 (br s, 2H). Dihydrochloride: light tan hygroscopic solid. $^1$H NMR (DMSO-d$_6$): 3.94 (s, 6H), 7.24 (s, 2H), 7.28 (d, 2H), 7.40 (br s, NHs), 7.46–7.51 (m, 4H), 9.43 (br s, 2H). MS (FAB, thioglycerol): m/z 395 (MH$^+$). Anal. Calcd. for C$_{20}$H$_{22}$N$_6$O$_3$·2.0HCl.1.0H$_2$O.0.1EtOH (489.98): C, H, N.

2,5-Bis(3-ethoxy-4-guanidinophenyl)furan (6d, DB779) was prepared according to the procedure for 6a using diamine 3j as starting material. Bis-Boc derivative: yellow solid. Yield: 76%. $^1$H NMR (CDCl$_3$): 1.50–1.54 (2s and t, 42H), 4.18, 4H), 6.63(s, 2H), 7.18(d, 2H), 7.36 (d, 2H), 8.57 (d, 2H), 11.02 (s, 2H), 11.58 (br s, 2H). Dihydrochloride: tan hygroscopic solid. $^1$H NMR (DMSO-d$_6$): 1.38 (t, 6H), 4.21 (q, 4H), 7.21 (d, 2H), 7.28 (dd, 2H), 7.42 (br s, NHs), 7.47 (m, 4H), 9.40 (br s, 2H). MS (ES): m/z 423 (MH$_+$). Anal. Calcd. for C$_{22}$H$_{26}$N$_6$O$_3$·2.0HCl.0.5H$_2$O (504.41): C, H, N.

2,5-Bis(4-guanidino-2-methylphenyl)thiophene (6e, DB752) was prepared according to the procedure for 6a using diamine 3k as starting material. Bis-Boc derivative: purification by silica gel chromatography (15% diethyl ether in hexanes) gave a yellow solid. Yield: 51%. $^1$H NMR (CDCl$_3$): 1.52–1.55 (2s, 36H), 2.47 (s, 6H), 7.00 (s, 2H), 7.41–7.44 (m, 4H), 7.58 (dd, 2H), 10.34 (s, 2H), 11.65 (br s, 2H). Dihydrochloride: tan/pale green hygroscopic solid. $^1$H NMR (DMSO-d$_6$): 2.46 (s, 6H), 7.12 (d, 2H), 7.20 (d, 2H), 7.24 (s, 2H), 7.50 (d, 2H), 7.56 (br s, NHs), 10.06 (br s, 2H). MS (ESI): m/z 379 [(M+H)$^+$, <1%], 190 [(M+2H)$^{2+}$, 100]. Anal. Calcd. for C$_{20}$H$_{22}$N$_6$S.2.0HCl.0.35H$_2$O (457.72): C, H, N.

2,5-Bis(4-guanidinophenyl)thiophene (6f, DB686) was prepared according to the procedure for 6a using 2,5-bis(4-aminophenyl)thiophene (See Ling, C. et al (1994) J. Am. Chem. Soc. 116:8784–8792, which is herein incorporated by reference) as starting material. Bis-Boc derivative: yellow solid. Yield: 70%. $^1$H NMR (CDCl$_3$): 1.54–1.57 (2s, 36H), 7.28 (s, 2H), 7.59 (d, 4H), 7.67 (d, 4H), 10.41 (br s, 2H). Dihydrochloride: yellow/pale green hygroscopic solid. $^1$H NMR (DMSO-d$_6$): 7.28 (d, 4H), 7.56 (s, 2H), 7.59 (br s, NHs), 7.74 (d, 4H), 10.14 (br s, 2H). MS (FAB, thioglycerol): m/z 351 (MH$^+$). Anal. Calcd. for C$_{18}$H$_{18}$N$_6$S.2.0HCl.0.5H$_2$O.0.2EtOH (441.59): C, H, N.

Additionally, the compounds of the invention include pharmaceutically acceptable salts, multimeric forms, prodrugs, active metabolites, precursors and salts of such metabolites of the reversed amidine compounds of the Structural Formulas described herein.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding (See, for example, Lee et al., (1984) Biochem. 23:4255). The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011–2016; Shan, D. et al., J. Pharm. Sci., 86(7):765–767; Bagshawe K., (1995) Drug Dev. Res. 34:220–230; Bodor, N., (1984) Advances in Drug Res. 13:224–331; Bundgaard, H., Design of Prodrugs (Elsevier Press, 1985); and Larsen, I. K., Design and Application of Prodrugs, Drug Design and Development (Krogsgaard-Larsen et al., eds., Harwood Academic Publishers, 1991).

If the reversed amidine compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the reversed amidine compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified structural formulas.

The anti-leishmanial activity of the reversed amidine compounds may be measured by any of the methods available to those skilled in the art, including in vitro and in vivo assays. Examples of suitable assays for activity measurements are provided herein. Properties of the reversed amidine compounds may be assessed, for example, by using one or more of the assays set out in the Examples below. Other pharmacological methods may also be used to determine the efficacy of the compounds as anti-leishmanial agents.

The reversed amidine compounds in accordance with the present invention are useful in the treatment of diseases, disorders and infections associated with organisms belonging to Leishmania such as *L. donovani, L. mexicana, L. tropica, L. aethiopica, L. peruviana, L. guyanensis, L. braziliensis, L. infantum*, and the like. The diseases, disorders and infections associated with Leishmania species include cutaneous, mucocutaneous, and visceral leishmaniasis, including manifestations of leishmaniasis co-presenting with another disease such as AIDS.

The reversed amidine compounds of the present invention may be used in combination with or as a substitution for treatments of the above conditions. For example, the reversed amidine compounds may also be used alone or combination with a supplementary active compound such as pentamidine or analogues thereof, sodium stibogluconate such as Pentostam®, meglumine antimoniate such as Glucantime®, amphotericin B, lipid complexed amphotericin B, miltefosine, paromomycin, and the like to treat, prevent or inhibit diseases, disorders and infections associated with Leishmania.

The reversed amidine compounds of the invention may be used alone or in combination with a supplementary active compound such as protease inhibitors or inhibitors of reverse transcriptase to treat Leishmania co-infection such as leishmaniasis-HIV co-infection.

A reversed amidine compound of the present invention may be administered in a therapeutically effective amount to a mammal such as a human. A therapeutically effective amount may be readily determined by standard methods known in the art. As used herein, a "therapeutically effective amount" of a reversed amidine compound of the present invention is an amount which prevents, inhibits, suppresses or reduces the amount of Leishmania amastigotes, promastigotes, or both in a subject as compared to a control. The therapeutically effective amount may be readily determined by conventional methods known in the art.

As defined herein, a therapeutically effective amount of a compound of the invention ranges from about 0.01 to about 100 mg/kg body weight, preferably about 0.1 to about 50 mg/kg body weight, and more preferably about 1 to about 10 mg/kg body weight. Preferred topical concentrations include about 0.1% to about 10% in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the reversed amidine compound preferably includes a single treatment, but can include a series of treatments.

In a preferred example, a subject is treated with a compound of the invention in the range of between about 1 to about 5 mg/kg body weight, at least once. The subject may treated with a compound of the invention in the range of between about 1 to about 5 mg/kg body weight from about one time per week to about once daily for about 5 to about 7 days or more. It will also be appreciated that the effective dosage of the compound used for treatment may increase or decrease over the course of a particular treatment. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given reversed amidine compound. Administration of prodrugs may be dosed at weight levels that are chemically equivalent to the weight levels of the fully active forms.

The reversed amidine compounds of the invention can be incorporated into pharmaceutical compositions suitable for administration. Pharmaceutical compositions of this invention comprise a therapeutically effective amount of a reversed amidine compound having the Structural Formula I, and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art.

Except insofar as any conventional media or agent is incompatible with the active compound, use thereof in the compositions is contemplated. Supplementary active compounds can also be incorporated into the compositions. Supplementary active compounds include sodium stibogluconate such as Pentostam®, meglumine antimoniate such as Glucantime®, pentamidine, amphotericin B, miltefosine, paromomycin and the like.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from 0–60% of the total volume. In an exemplary embodiment, the reversed amidine compound of the present invention is dissolved in DMSO and diluted with water.

The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may comprise formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating the reversed amidine compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., comprising conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The following examples are intended to illustrate but not to limit the invention.

EXAMPLE 1

Axenic Amastigote Assay

The growth susceptibilities of *L. donovani* axenic amastigote-like parasites to the candidate compounds were measured in a three day assay using the tetrazolium dye-based CellTiter 96 Aqueous Non-Radioactive Cell Proliferation Assay Kit (Promega, Madison, Wis.) according to Werbovetz, K., et al. (1999) *Mol. Biochem. Parasitol.* 98:53–65, which is herein incorporated by reference. Pentamidine, at a starting concentration of 100 µM, and serial dilutions thereof were used as controls. Specifically, *L. donovani* axenic amastigotes, as described by Joshi, M. et al. (1993) Mol. Biochem. Parasitol. 58:345–354, which is herein incorporated by reference, were seeded at $10^6$ cells/ml in 96-well flat-bottomed plates (Costar, Cambridge, Mass.) and maintained as axenic amastigote-like forms by serial passage at 37° C. in a humid atmosphere comprising 5% $CO_2$ using a slightly modified potassium-based version of the medium described by Joshi, M. et al. (1993) in the presence or absence of a given candidate compound. The medium comprised 15 mM KCl, 115 mM $KH_2PO_4$, 10 mM $K_2HPO_4$, 0.5 mM $MgSO_4$, and 24 mM $NaHCO_3$ to give a final potassium concentration of 140 mM. The medium was supplemented with 20% fetal bovine serum and was brought to pH 5.5. The final volume in each well was 60 µl. The plates were incubated at 37° C. for 72 hours, then 12 µl of the aqueous CellTiter solution from the kit (Promega, Madison, Wis.) was added to each well according to the instructions of the manufacturer. The plates were returned to the incubator for about 2 to about 3 hours. Then the absorbance of each well was measured at 490 nm using a SpectraMax Plus microplate reader (Molecular Devices, Sunnyvale, Calif.).

Figure 2:
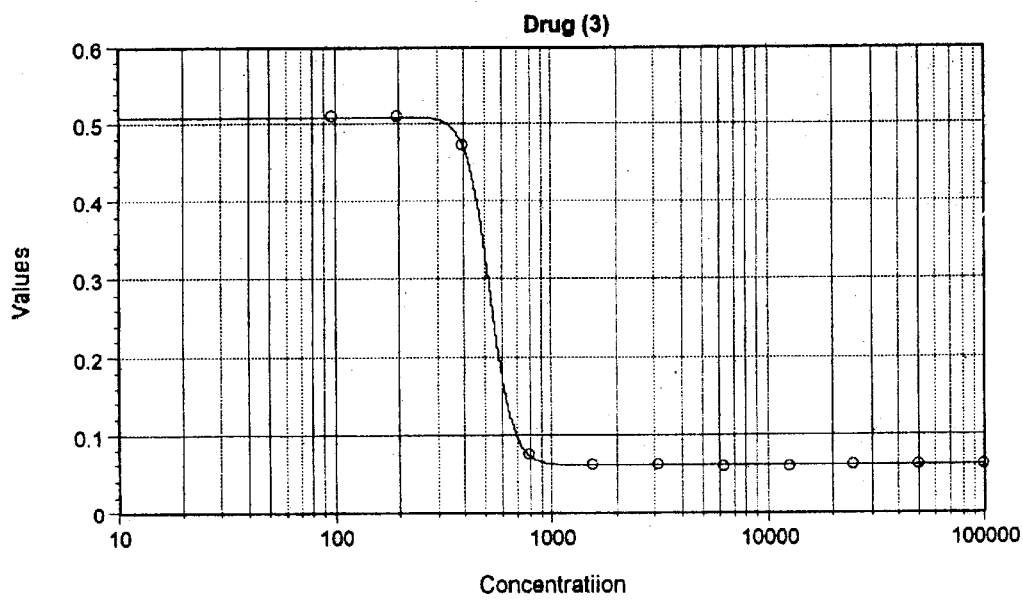
FIG. 2 provides the graphical data obtained for compound 1DWB667 in the amastigote drug assay.

The results for each candidate compound may be found in the FIG. 1. The $IC_{50}$ values (the concentration of the agent that inhibited parasite growth by 50%) for each candidate compound were determined for axenic amastigotes with the aid of the program SoftMax Pro (Molecular Devices, Sunnyvale, Calif.) using the following dose response equation: $y=((a-d)/1+(x/c)^b)+d$, wherein x=drug concentration; y=absorbance at 490 nm; a=upper asymptote; b=slope; c=$IC_{50}$; and d=lower asymptote. FIG. 2 is the graphical data obtained for compound 1DWB667 as an example.

As shown in FIG. 1, DB 702, DB 709, DB 710, DB 710, DB 712, DB 713, and DB 714 were from about 2 to about 5 fold more active against axenic amastigotes that the prototype compound, 1DWB667. When compared to pentamidine, these compounds were about five to about 12 fold more active against amastigotes.

After testing a compound in this axenic amastigote-screening assay, selected compounds having an $IC_{50}$ of 10 µg/ml or less were tested in the infected macrophage assay below.

EXAMPLE 2

Infected Macrophage Assay

The susceptibilities of *L. mexicania* infected macrophages to candidate compounds were determined by the following assay. Amphotericin B was used as a control instead of pentamidine since pentamidine is ineffective in the macrophage model.

A one week old, confluent culture of J774.G8 mouse macrophages was washed three times with Hank's Balanced Salt Solution (HBSS) without calcium and magnesium (Sigma, St. Louis, Mo.). The J774.G8 mouse macrophages are a continuous cell line that have been cited in the literature as supporting continuous and intracellular growth of various Leishmania sp. and they have been used for drug assays against intracellular parasites, *Trypanosoma cruzi* and Leishmania sp. See Alcina, A., et al. (1988) Antimicrobial Agents & Chemotherapy. 32(9):1412–5; Mendez, S., et al. (1996) International Journal for Parasitology 26(6):619–22; Hodgkinson, V. H., et al. (1996) Experimental Parasitology 83(1):94–105; and Chang, K. P. (1980) Science 209(4462): 1240–42, which are herein incorporated by reference.

The macrophages were then incubated at 37° C. in a humidified 5% $CO_2$ incubator for 15 minutes with a Trypsin-EDTA (0.05% Trypsin, 0.53 mM EDTA 4Na) solution (GIBCO BRL, Grand Island, N.Y.). The macrophages were then detached with a cell scraper and suspended by vigorous pipetting. The macrophages were then mixed with a late log phase culture of *L. mexicana* promastigotes to yield a solution comprising about $5 \times 10^5$ macrophages per ml and about $25 \times 10^5$ promastigotes per ml in DMEM (pH 7.4) supplemented with 10% heat inactivated fetal calf serum comprising penicillin (50 units/ml) and streptomycin (50 µg/ml).

The macrophage-parasite mixture was then pipetted into 96-well flat-bottom plates (Costar, Cambridge, Mass.) at 200 µl per well. Infection and attachment of the macrophages was allowed to occur over a period of about 48 hours at 33° C. in a humidified 5% $CO_2$ incubator. The wells were washed three times with HBSS to remove extracellular parasites. Each well was then treated with serial dilutions of a given candidate compound in DMEM.

The treated plate was incubated for about 72 hours at 33° C. in a humidified 5% $CO_2$ incubator. The macrophages in each well were detached into the DMEM used for the incubation by pipetting and scraping with the tip of a microliter pipettor. 75 µl of the cell suspension was transferred to a cytospin funnel and the cells were centrifuged onto microscope slides at 800 rpm for 5 minutes using a Cytospin centrifuge (Shandon, Pittsburgh, Pa.).

The slides were air dried and then fixed in methanol for 5 seconds. After the methanol evaporated, the slides were stained with 5% Giemsa stain (Fisher, Suwanee, Ga.) in phosphate buffer comprising 3.1 mM potassium phosphate dibasic and 8.3 mM sodium phosphate monobasic for 45 minutes. After thorough washing with flowing tap water, the slides were air dried and then viewed by oil immersion microscopy to determine percentage of infected cells. A cell was considered to be infected if it comprised one or more amastigote with a visible parasite nucleus and kinetoplast. Counting parasites and counting infected cells provided similar results when determining $IC_{50}$ values.

Figure 3:
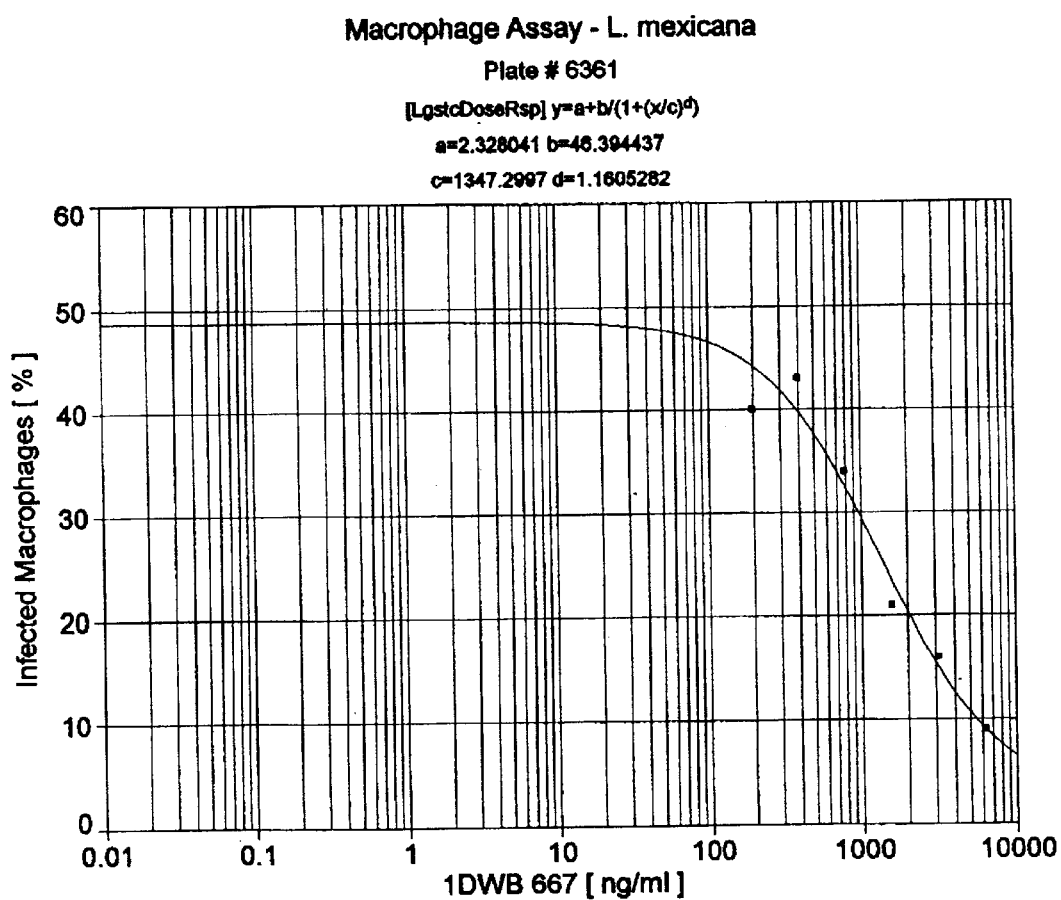
FIG. 3 provides the graphical data obtained for compound 1DWB667 in the L. mexicana macrophage assay.

The $IC_{50}$ values (the concentration of the compound that inhibited the number of infected macrophages by 50%) were determined with the software program TableCurve (SPSS Science, Chicago, Ill.) using the following dose-response equation: $y=a+b/(1+(x/c)^d)$, where x=the drug concentration, y=absorbance at 490 nm, a=upper asymptote, b=slope, c=$IC_{50}$ and d=lower asymptote. FIG. 3 provides the graphical data obtained for compound 1DWB667 as an example.

Figure 4:
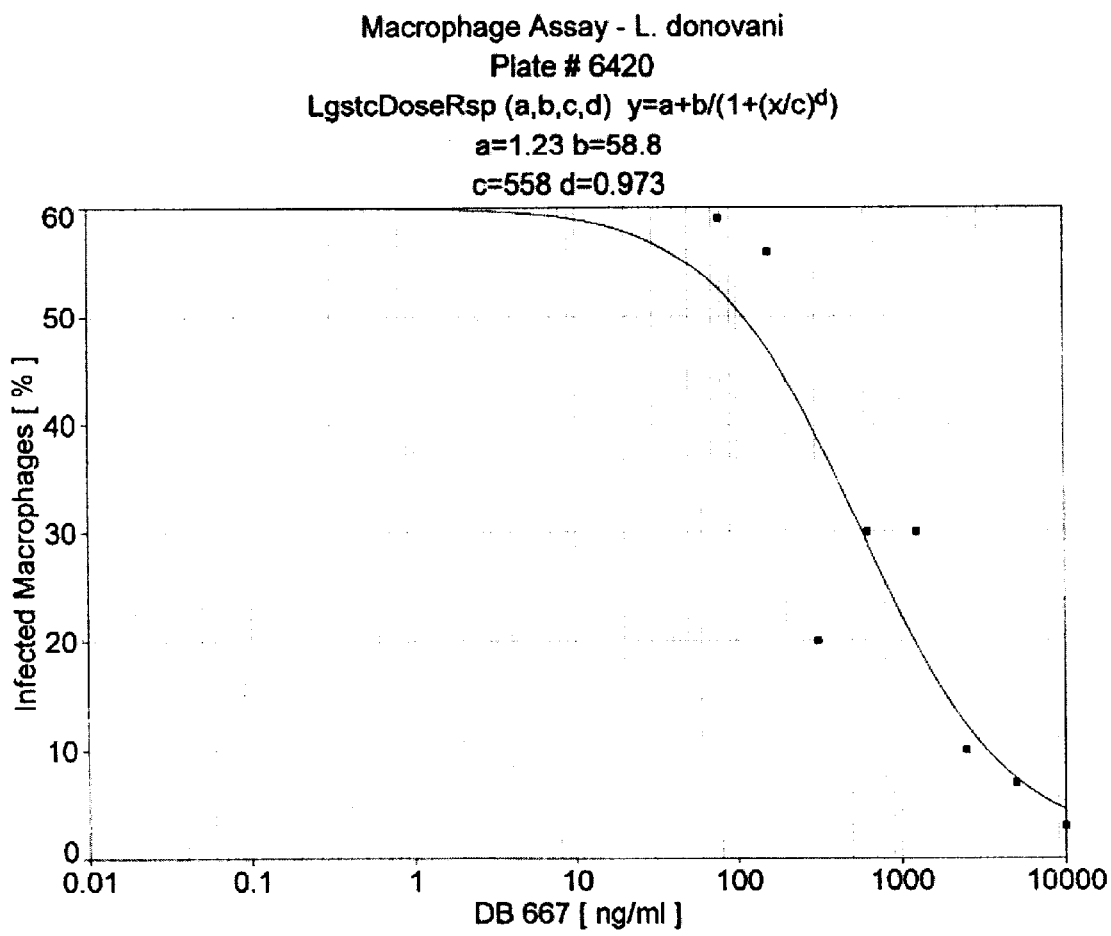
FIG. 4 provides the graphical data obtained for compound 1DWB667 in the L. donovani macrophage assay.

The susceptibility of L. donovani infected macrophages to the compounds of the present invention were preformed by a modified protocol for L. mexicana infected macrophages above, wherein all incubations of the parasite infected macrophages were done at 37° C. rather than 33° C. FIG. 4 provides the graphical data for compound 1DWB667 as an example.

Table 1 below compares the $IC_{50}$'s for selected compounds.

TABLE 1

|  | Axenic Amastigote $IC_{50}$ (µg/ml) L. donovani | Macrophage $IC_{50}$ (µg/ml) L. donovani | Macrophage $IC_{50}$ (µg/ml) L. mexicana |
| --- | --- | --- | --- |
| Pentamidine | 1.22 | Not tested | >12.5 |
| Amphotericin B | 0.342 | 0.024 | 0.032 |
| 1DWB 667 | 0.550 | 0.942 | 1.37 |
| DB 702 | 0.174 | 0.063 | 0.220 |
| DB 709 | 0.157 | 0.104 | 0.127 |
| DB 710 | 0.242 | 0.530 | 0.094 |
| DB 712 | 0.308 | 0.127 | 0.689 |
| DB 713 | 0.324 | 0.385 | 0.371 |
| DB 714 | 0.290 | 0.246 | 0.359 |

The data in FIG. 1 shows that the reversed amidines are more potent antiparasitic agents that the prototype compound, 1DWB667, in the L. mexicana infected macrophages and the L. donovani infected macrophages. DB 712 was the least effective in reducing parasite burden in the macrophage for both the cutaneous and visceral strains of parasite.

The results for each candidate compound may be found in FIG. 1.

EXAMPLE 3

Macrophage Toxicity Assay

The toxicity of the candidate compounds on J774.G8 macrophages was measured using a sulforhodamine B (Molecular Probes, Eugene, Oreg.) based dye assay.

Specifically, a confluent culture of macrophages in a T75 culture flask was harvested by replacing the growth medium (DMEM supplemented with 10% heat inactivated fetal calf serum, 50 units/ml penicillin, and 50 µg/ml streptomycin) with 25 ml of fresh medium and scraping the cells from the bottom of the culture flask. Cell clumps were broken up by gentle pipetting and the cell suspension was transferred to a 50 ml conical centrifuge tube. The cells were then pelleted by centrifugation at 1,000 rpm at 4° C. for 5 minutes. The supernatant was then removed and the cells were resuspended in 15 ml DMEM.

After counting an aliquot of the cell suspension, the macrophages were then diluted to about $1 \times 10^5$ cells/ml in DMEM and 180 µl was added to each well of a 96 well tissue culture plate Then 20 µl serial dilutions of a given candidate compound was added. The plate was then placed in a 37° C. humidified 5% $CO_2$ incubator and incubated for 72 hours. Then 50 µl of 50% TCA was added to each well to fix the proteins. The plate was then incubated for at least 1 hour at 4° C.

The liquid contents of the wells were discarded and the wells were washed five times with 200 µl of distilled water. After the final wash the plate was allowed to air dry for 20 minutes. 100 µl of the sulforhodamine B dye (0.4% dye in 1% acetic acid) was added. The plate was then incubated at room temperature for 20 minutes. After discarding the dye solution, the wells were washed five times with 200 µl of 1% acetic acid and then allowed to air dry for 20 minutes. At this time, 50 µl of 10 mM TRIS base was added. After a few minutes of incubation, the absorbance of each well at 490 nm was measured in a SpectraMax Pro microplate reader (Molecular Devices, Sunnyvale, Calif.).

Figure 5:
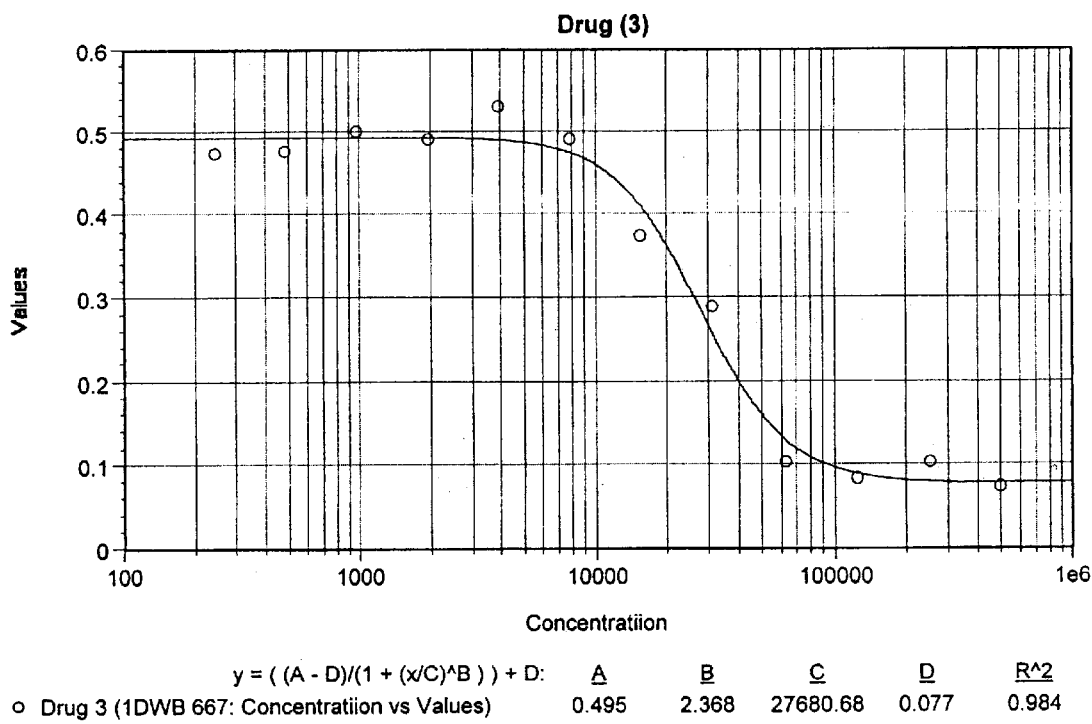
FIG. 5 provides the graphical data obtained for compound 1DWB667 in the macrophage toxicity assay.

The $IC_{50}$ values for each candidate compound (the concentration of the agent that inhibited macrophage growth by 50%) were determined for the macrophages with the aid of the program SoftMax Pro (Molecular Devices, Sunnyvale, Calif.) using the following dose response equation: $y=((a-d)/1+(x/c)^b)+d$, where x=drug concentration; y=absorbance at 490 nm; a=upper asymptote; b=slope; c=$IC_{50}$; and d=lower asymptote. FIG. 5 provides the graphical data for compound 1DWB667 as an example.

Table 2 below shows the results for a few selected compounds.

TABLE 2

|  | $IC_{50}$ (µg/ml) |
| --- | --- |
| Pentamidine | 9.96 |
| 1DWB 667 | 4.28 |
| DB 702 | 2.23 |
| DB 709 | 0.199 |
| DB 710 | 3.64 |
| DB 712 | 3.39 |

DB 709 was the only compound of those tested that was toxic to the macrophage in vitro within the same range of toxicity to the amastigote within the macrophage $IC_{50}$= 0.104 µg/ml for L. donovani-infected macrophages and $IC_{50}$=0.127 µg/ml for L. mexicana-infected macrophages.

The toxicity of DB 710 and DB 712 to the macrophage was about less than or equal to DB 702 and 1DWB667 when compared with pentamidine. The results for each candidate compound may be found in FIG. 1.

It is important to note that one cannot compare the relative toxicity between different classes of compounds. However, one can compare the toxicity of compounds comprising similar structures and use such comparisons in further studies. See Phillips, J. C. et al. (1990) Fd. Chem. Tox. 28(5):375–394, which is herein incorporated by reference.

EXAMPLE 4

In vivo Assay of Reverse Amidines

In vivo testing of the reversed amidines was conducted in a murine model of leishmaniasis. See Smith, A. et al. (2000) Antimicrob. Agents Chemother. 44:1494, which is herein incorporated by reference. In the visceral model of leishmaniasis, BALB/c mice (female, about 18–20 g each) were infected i.v. with metacyclic *Leishmania donovani* amastigotes from the spleen of a donor hamster, however, the mice may be infected with promastigotes i.p. Dosing with a given reversed amidine or a control began at about 7 to about 10 days post-infection and continued at one dose per day for about four to about five days. On day 14 the mice were sacrificed. The liver and spleens were weighed and impression smears prepared. The smears were fixed in 100% methanol and stained with 10% Giemsa. The percent suppression of amastigote numbers compared to controls is determined using the formula: # of amastigotes/500 liver cells×liver (spleen) weight×200,000. The controls were Pentostam® and pentamidine. The results are provided in the following Tables 3 and 4:

TABLE 3

In vivo Activity of DB 516, DB 667, and DB 680 Against *L. donovani* L82

| Compound | Dosing Regimen | Actual Total Dose Received | % Inhib. ± SEM |
|---|---|---|---|
| Pentostam ® | 15 mg Sb(V)/kg s.c. × 5 | 7.5 mg Sb(V) | 60.4 ± 4.6 |
| Pentamidine[a] | 5 mg/kg i.v. × 5 | 1.5 mg | 30.5 ± 5.0 |
| DB 667[b] | 5 mg/kg i.v. × 5 | 2.5 mg | NA |
| DB 680[c] | 5 mg/kg i.v. × 5 | 0.5 mg | 55.0 ± 5.5 |

[a]Produced irritation on administration of full dose on day 1. Dose reduced by 50% for all mice for the following 4 days.
[b]all mice dead within 30 minutes of dosing on day 1.
[c]2 of 5 mice given half dose. All mice given half dose for the following 4 days.

TABLE 4

In vivo Activity of DB 680, DB 712, and DB 686, and DB746 Against *L. donovani* L82

| | Dosing regimen | Total dose per mouse | % inhibition ± S.E.M. |
|---|---|---|---|
| Pentostam ® | 15 mg Sb$^v$/kg s.c. × 5 | 1.5 mg | 47.74 ± 5.2 |
| Pentamidine | 4 mg/kg i.v. × 5 | 0.4 mg | 16.96 ± 3.3 |
| DB680 | 4 mg/kg i.v. × 5 | 0.4 mg | 28.73 ± 2.0 |
| DB712 | 15 μmol/kg i.v. × 5 | 1.5 μmol | 15.33 ± 2.7 |
| DB686 | 10 mg/kg p.o. × 5 | 1.0 mg | 34.91 ± 8.04 |
| DB746 | 10 mg/kg p.o. × 5 | 0.4 mg* | 24.24 ± 3.9 |

*Effects observed with DB746
Day 1: Tremors and hyperactivity within 10 minutes.
Day 2: Severe tremors, hyperactivity and loss of motor control.
Day 3: No further dosing due to continuing symptoms as above.

Since DB 680 showed good in vivo activity, this compound was examined in further detail. The results are provided in the following Table 5:

TABLE 5

In vivo Activity of DB 680 Against L. donovani L82

| Compound | Dosing Regimen | Total Dose per Mouse | % Inhib. ± SEM |
|---|---|---|---|
| Pentamidine | 4 mg/kg i.v. × 5 | 4 mg (0.68 mM) | 30.6 ± 5.2 |
| DB 680 | 2.5 mg/kg i.v. × 5 | 0.25 mg (0.51 mM) | 44.0 ± 0.9 |
| DB 680 | 0.83 mg/kg i.v. × 5 | 0.83 mg (0.17 mM) | 39.6 ± 5.2 |
| DB 680 | 0.27 mg/kg i.v. × 5 | 0.027 mg (0.055 mM) | 35.1 ± 4.0 |
| DB 680 | 50 mg/kg oral × 5 | 0.5 mg (10.15 mM) | 48.6 ± 3.2 |
| DB 680 | 16.7 mg/kg oral × 5 | 1.67 mg (3.38 mM) | 53.2 ± 4.7 |

[a]Produced irritation on administration of full dose on day 1. Dose reduced by 50% for all mice for the following 4 days.
[b]all mice dead within 30 minutes of dosing on day 1.
[c]2 of 5 mice given half dose. All mice given half dose for the following 4 days.

Thus, the compounds of the present invention are effective for treating leishmaniasis in subjects.

In the cutaneous model, BALB/c mice are infected with *Leishmania mexicana* promastigotes or amastigotes s.c. at the base of the back. Dosing with a given reversed amidine or a control begins when the lesion has developed to about 4 to about 6 mm diameter, just prior to ulceration. After this dosing period, the size of the lesion is measured weekly in two dimensions (mean recorded) using calipers for about 6 to about 8 weeks. The percent increase or decrease in lesion size is determined weekly.

The controls may be Pentostam® and pentamidine.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for treating or inhibiting leishmaniasis in a subject in need thereof comprising administering to the subject a therapeutically effective amount of at least one compound having the structural formula

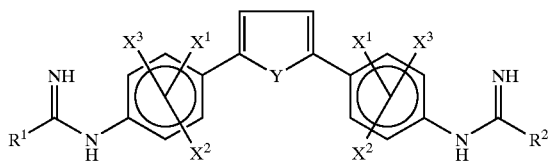

wherein Y is a heteroatom;

$R^1$ and $R^2$ are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group.

2. The method of claim 1, wherein Y is O or S.

3. The method of claim 1, wherein $R^1$ and $R^2$ are independently H, phenyl, cyclohexyl, quinolyl, pyridinyl, amino, or methylpyridinyl.

4. The method of claim 1, wherein $X^1$, $X^2$, and $X^3$ are independently H, Cl, methyl, amino, methoxy, ethoxy, or propan-2-oxy.

5. The method of claim 1, wherein $X^1$, $X^2$, and $X^3$ are each independently at positions 2, 3, 5, or 6 of the phenyl rings.

6. The method of claim 1, wherein $X^1$ and $X^2$ are each independently at positions 2 or 3 of the phenyl rings.

7. The method of claim 1, further comprising administering a supplementary active compound.

8. The method of claim 7, wherein the supplementary active compound is sodium stibogluconate, meglumine antimonite, pentamidine, amphotericin B, miltefosine, or paromomycin.

9. The method of claim 1, wherein the compound is 2,5-Bis[4-(2-pyridylimino)aminophenyl]furan;
2,5-Bis[4-(benzimidoylamino)phenyl]furan;
2,5-Bis[4-(cyclohexylimino)aminophenyl]furan;
2,5-Bis[4-(acetimidoyl)aminophenyl]furan;
2,5-Bis[4-(benzimidoyl)amino-2-methylphenyl]furan;
2,5-Bis[2-methyl-4-(2-pyridylimino)aminophenyl]furan;
2,5-Bis[2-methyl-4-(2-quinolylimino)aminophenyl]furan;
2,5-Bis[2-methyl-4-(5-methyl-2-pyridylimino)aminophenyl]furan;
2,5-Bis[2-methoxy-4-(2-pyridylimino)aminophenyl]furan;
2,5-Bis[2-chloro-4-(2-pyridylimino)aminophenyl]furan;
2,5-Bis[2,6-dimethyl-4-(2-pyridylimino)aminophenyl]furan;
2,5-Bis(4-guanidino-2-methylphenyl)furan;
2,5-Bis(4-guanidino-2-trifluoromethylphenyl)furan;
2,5-Bis[2-methyl-4-(2-pyridylimino)aminophenyl]thiophene;
2-[5(6)-(2-Pyridylimino)amino-2-benzimidazoyl]-5-[4-(2-pyridylimino)aminophenyl]furan;
2,5-Bis[2-methyl-4-(2-quinolylimino)aminophenyl]furan;
2-(4-Guanidinophenyl)-4-(3-guanidinophenyl)furan;
2,5-Bis(4-guanidino-2,6-dimethylphenyl)furan;
2,5-Bis[2-ethoxy-4-(2-pyridylimino)aminophenyl)furan;
2,5-Bis[2,3-dimethyl-4-(2-pyridylimino)aminophenyl]furan;
2,5-Bis(4-guanidino-2,3-dimethylphenyl)furan;
2,5-Bis[2-methyl-4-(6-methyl-2-pyridylimino)aminophenyl]furan;
2,5-Bis[2-hydroxy-4-(2-pyridylimino)aminophenyl]furan;
2,5-Bis[2-methoxy-5-(2-pyridylimino)aminophenyl]furan;
2,5-Bis[2-(2-propoxy)-4-(2-pyridylimino)aminophenyl]furan;
2,5-Bis[2-(2-propoxy)-4-(5-methyl-2-pyridylimino)aminophenyl]furan;
2,5-Bis[3-ethoxy-4-(2-pyridylimino)aminophenyl]furan;
2,5-Bis(2-ethoxy-4-guanidinophenyl)furan;
2,5-Bis[4-guanidino-2-(2-propoxy)phenyl]furan;
2,5-Bis(4-guanidino-3-methoxyphenyl)furan;
2,5-Bis(3-ethoxy-4-guanidinophenyl)furan;
2,5-Bis[3-methoxy-4-(2-pyridylimino)aminophenyl]furan
2,5-Bis(4-guanidino-2-methylphenyl)thiophene; or
2,5-Bis(4-guanidinophenyl)thiophene.

10. A method for treating or inhibiting leishmaniasis in a subject in need thereof comprising administering to the subject a therapeutically effective amount of at least one reversed amidine.

11. A method for treating or inhibiting leishmaniasis in a subject in need thereof comprising administering to the subject a therapeutically effective amount of at least one compound comprising at least one reversed amidine group having the structural formula

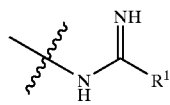

wherein R¹ is H or an alkyl, cycloalkyl, heterocycloalkyl, aryl, amino or heteroaryl group.

12. A method for treating or inhibiting a disease or disorder associated with leishmaniasis in a subject in need thereof comprising administering to the subject a therapeutically effective amount of at least one compound having the structural formula

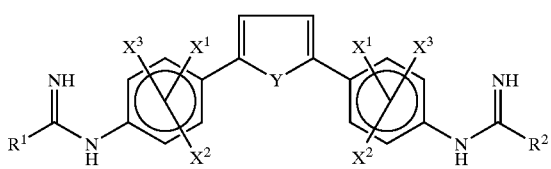

wherein Y is a heteroatom;

R¹ and R² are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group.

13. The method of claim 12, wherein Y is O or S.

14. The method of claim 12, wherein R¹ and R² are independently H, phenyl, cyclohexyl, quinolyl, pyridinyl, amino, or methylpyridinyl.

15. The method of claim 12, wherein $X^1$, $X^2$, and $X^3$ are independently H, Cl, methyl, amino, methoxy, ethoxy, or propan-2-oxy.

16. The method of claim 12, wherein $X^1$, $X^2$, and $X^3$ are each independently at positions 2, 3, 5, or 6 of the phenyl rings.

17. The method of claim 12, wherein $X^1$ and $X^2$ are each independently at positions 2 or 3 of the phenyl rings.

18. The method of claim 12, wherein the disease or disorder is cutaneous leishmaniasis, mucocutaneous leishmaniasis, or visceral leishmaniasis.

19. A method of reducing, suppressing or inhibiting a Leishmania parasite in a target comprising administering to the target an effective amount of at least one compound having the structural formula

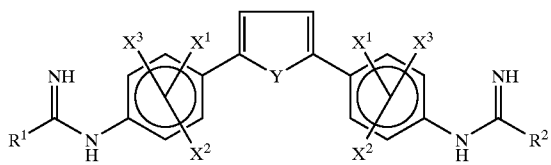

wherein Y is a heteroatom;

R¹ and R² are independently H or an alkyl, cycloalkyl, heterocycloalkyl, aryl, amino or heteroaryl group; and $X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group.

20. The method of claim 19, wherein the Leishmania parasite is *L. mexicana*.

21. The method of claim 19, wherein the Leishmania parasite is *L. donovani*.

22. The method of claim 19, wherein the compound reduces, suppresses or inhibits the Leishmania parasite by about 50% at a concentration of about 10.0 µg/ml or less.

23. The method of claim 19, wherein the compound reduces, suppresses or inhibits the Leishmania parasite by about 50% at a concentration of about 7.0 µg/ml or less.

24. The method of claim 19, wherein the compound reduces, suppresses or inhibits the Leishmania parasite by about 50% at a concentration of about 5.0 µg/ml or less.

25. The method of claim 19, wherein the compound reduces, suppresses or inhibits the Leishmania parasite by about 50% at a concentration of about 2.5 µg/ml or less.

26. The method of claim 19, wherein the compound reduces, suppresses or inhibits the Leishmania parasite by about 50% at a concentration of about 1.0 µg/ml or less.

27. The method of claim 19, wherein the compound reduces, suppresses or inhibits the Leishmania parasite by about 50% at a concentration of about 0.1 µg/ml.

28. The method of claim 19, wherein the target a mammal or a tissue or a cell derived therefrom.

29. A kit comprising a comprising at least one compound having the structural formula

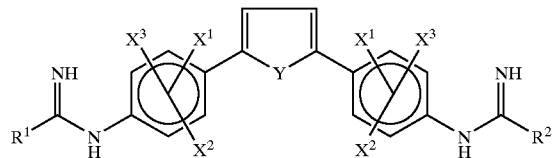

wherein Y is a heteroatom;

R¹ and R² are independently H or an alkyl, cycloalkyl, heterocycloalkyl, aryl, amino or heteroaryl group;

$X^1$, $X^2$, and $X^3$ are independently H or an alkyl, alkoxy, halo, amino, alkylamino, dialkylamino, acylamino, alkylthio, sulfonyl, cyano, carboxy, alkoxycarbonyl, or carbamoyl group; and instructions for use of the compound for the treatment of a subject having a disease or disorder associated with leishmaniasis.

* * * * *